United States Patent
Saitoh et al.

(10) Patent No.: US 7,229,702 B2
(45) Date of Patent: Jun. 12, 2007

(54) OLIGOFLUORENLYLENE COMPOUNDS

(75) Inventors: Akihito Saitoh, Kanagawa (JP); Mizuho Hiraoka, Kanagawa (JP); Koichi Suzuki, Kanagawa (JP); Akihiro Senoo, Kanagawa (JP); Hiroshi Tanabe, Kanagawa (JP); Naoki Yamada, Tokyo (JP); Chika Negishi, Kanagawa (JP); Maki Okajima, Tokyo (JP)

(73) Assignee: Canon Kabushiki Kaisha, Tokyp (JP)

( * ) Notice: Subject to any disclaimer, the term of this patent is extended or adjusted under 35 U.S.C. 154(b) by 337 days.

(21) Appl. No.: 10/506,300

(22) PCT Filed: Mar. 25, 2003

(86) PCT No.: PCT/JP03/03615

§ 371 (c)(1), (2), (4) Date: Sep. 1, 2004

(87) PCT Pub. No.: WO03/080559

PCT Pub. Date: Oct. 2, 2003

(65) Prior Publication Data

US 2005/0106414 A1 May 19, 2005

(30) Foreign Application Priority Data

Mar. 27, 2002 (JP) ............... 2002-088918
Jan. 15, 2003 (JP) ............... 2003-006796

(51) Int. Cl.
H01L 51/54 (2006.01)
C07C 211/61 (2006.01)
C09K 11/06 (2006.01)

(52) U.S. Cl. ............ 428/690; 428/917; 313/504; 313/506; 257/40; 257/E51.027; 257/E51.051; 564/427

(58) Field of Classification Search ............ None
See application file for complete search history.

(56) References Cited

U.S. PATENT DOCUMENTS

| | | | |
|---|---|---|---|
| 5,130,603 A | 7/1992 | Tokailin et al. | 313/504 |
| 5,151,629 A | 9/1992 | VanSlyke | 313/504 |
| 5,317,169 A | 5/1994 | Nakano et al. | 257/40 |
| 5,726,457 A | 3/1998 | Nakano et al. | 257/40 |
| 6,093,864 A | 7/2000 | Tokailin et al. | 585/25 |
| 6,100,405 A | 8/2000 | Reinhardt et al. | 548/160 |
| 6,280,859 B1 * | 8/2001 | Onikubo et al. | 428/690 |
| 6,362,310 B1 * | 3/2002 | Woo et al. | 528/397 |
| 6,387,544 B1 | 5/2002 | Thompson et al. | 428/690 |
| 6,517,957 B1 | 2/2003 | Senoo et al. | 428/690 |
| 6,743,948 B1 | 6/2004 | Hosokawa et al. | 564/426 |
| 6,777,531 B2 * | 8/2004 | Yasuda et al. | 528/422 |
| 6,916,555 B2 * | 7/2005 | Suzuki et al. | 428/690 |
| 2001/0051487 A1 | 12/2001 | Hashimoto et al. | 445/24 |
| 2003/0072966 A1 | 4/2003 | Hosokawa et al. | 428/690 |

FOREIGN PATENT DOCUMENTS

| | | |
|---|---|---|
| EP | 0 525 739 | 2/1993 |
| EP | 0 879 868 | 11/1998 |
| JP | 02-247278 | 10/1990 |
| JP | 03-255190 | 11/1991 |
| JP | 04-145192 | 5/1992 |
| JP | 05-202356 | 8/1993 |
| JP | 05-247460 | 9/1993 |
| JP | 09-202878 | 8/1997 |
| JP | 09-227576 | 9/1997 |
| JP | 2001-39933 | 2/2001 |
| JP | 2001-52868 | 2/2001 |
| WO | 00/33617 | 6/2000 |

OTHER PUBLICATIONS

Machine assisted translation of JP 2001-039933.*
Translation of Official Action dated Mar. 18, 2005 issued in Chinese Application No. 038012987 and Official Action.
Burroughs et al., "Light-emitting Diodes Based on Conjugated Polymers", *Nature*, vol. 347, 1990, pp. 539-541.
Tang et al., "Organic Electroluminescent Diodes", *Appl. Phys. Lett.*, vol. 51, No. 12, 1987, pp. 913-915.
Patent Abstracts of Japan, vol. 2000, No. 19, Jun. 5, 2001 (corresponds to JP 2001-39933).

* cited by examiner

*Primary Examiner*—Marie Yamnitzky
*Assistant Examiner*—Brett A. Crouse
(74) *Attorney, Agent, or Firm*—Fitzpatrick, Cella, Harper & Scinto

(57) ABSTRACT

The present invention provides an oligofluorenylene compound represented by the general formula below, which enables production of an organic light-emitting device that exhibits an extremely pure luminescent hue and has a light emission of high efficiency, high brightness, and long lifetime.

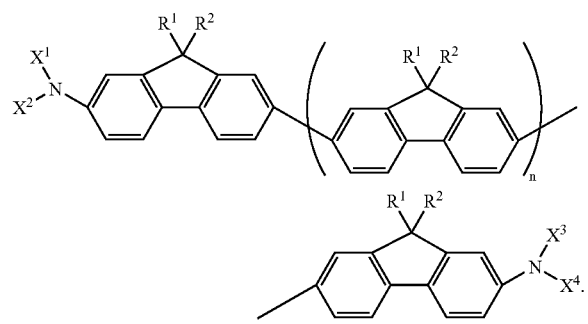

3 Claims, 2 Drawing Sheets

OLIGOFLUORENLYLENE COMPOUNDS

This is a national phase entry of PCT/JP03/03615 filed Mar. 25, 2003.

TECHNICAL FIELD

The present invention relates to an oligofluorenylene compound. Also, the invention relates to an organic light-emitting device comprising the compound, and more specifically, a device that emit light by applying an electric field to a thin film composed of an organic compound.

BACKGROUND ART

Organic light-emitting devices are devices that utilize light emitted when excitons of fluorescent organic compounds return to the ground state, the excitons being generated by sandwiching between an anode and a cathode a thin film that contains a fluorescent compound and injecting electrons and holes (positive holes) from the respective electrodes.

A study by Eastman Kodak Company in 1987 (Non-patent reference 1) has reported that a light emission of about 1000 cd/m$^2$ was observed under an applied voltage of about 10 V. In the study, the device had a separated-function type bilayer structure and used ITO as the anode, magnesium-silver alloy as the cathode, an aluminum quinolinol complex as an electron-carrying material and light-emitting material, and a triphenylamine derivative as a hole-carrying material. Related patent documents include the patent references 1 to 3.

Moreover, various light emissions from ultraviolet to infrared can be accomplished by using various different fluorescent organic compounds. Recently, active studies have been conducted on various compounds. Such studies are disclosed, for example, in the Patent references 4 to 11.

In addition to the organic light-emitting devices using small molecular materials as described above, organic light-emitting devices using conjugated polymers have been reported by a group of Cambridge University (non-patent reference 2). This report has disclosed that a film of polyphenylenevinylene (PPV) was formed by a coating method and it was confirmed that a single layer of the film emitted light. Related patent documents on organic light-emitting devices using conjugated polymers include the patent references 12 to 16.

As described above, a remarkable progress has been made in the field of organic light-emitting devices. The characteristic feature of such progress is that it enables production of light-emitting devices that exhibit high brightness even with a low application voltage, diversity in terms of emission wavelengths, and rapid response, with a thin and lightweight construction, which suggests a wide range of possible applications of the devices.

There are, however, still many problems with regard to durability, such as change with time due to prolonged use and deterioration due to moisture and the atmospheric gas containing oxygen. Moreover, for applications to a full-color display etc., light emissions exhibiting higher brightness or higher conversion efficiency, as well as blue, green, and red light emissions with higher color purities, are necessary with the current state of the art. For example, the patent reference 17 discloses diamine compounds as high emission efficiency materials, but blue-light emission showing high color purity (chromaticity coordinates: (x, y)=(0.14-0.15, 0.09-0.12)) has not been obtained yet.

(Patent Reference 1)
U.S. Pat. No. 4,539,507
(Patent Reference 2)
U.S. Pat. No. 4,720,432
(Patent Reference 3)
U.S. Pat. No. 4,885,211
(Patent Reference 4)
U.S. Pat. No. 5,151,629
(Patent Reference 5)
U.S. Pat. No. 5,409,783
(Patent Reference 6)
U.S. Pat. No. 5,382,477
(Patent Reference 7)
Japanese Patent Application Laid-Open No. 2-247278
(Patent Reference 8)
Japanese Patent Application Laid-Open No. 3-255190
(Patent Reference 9)
Japanese Patent Application Laid-Open No. 5-202356
(Patent Reference 10)
Japanese Patent Application Laid-Open No. 9-202878
(Patent Reference 11)
Japanese Patent Application Laid-Open No. 9-227576
(Patent Reference 12)
U.S. Pat. No. 5,247,190
(Patent Reference 13)
U.S. Pat. No. 5,514,878
(Patent Reference 14)
U.S. Pat. No. 5,672,678
(Patent Reference 15)
Japanese Patent Application Laid-Open No. 4-145192
(Patent Reference 16)
Japanese Patent Application Laid-Open No. 5-247460
(Patent Reference 17)
Japanese Patent Application Laid-Open No. 2001-52868
(Non-Patent Reference 1)
Appl. Phys. Lett. 51, 913 (1987)
(Non-Patent Reference 2)
Nature, 347, 539 (1990)

DISCLOSURE OF THE INVENTION

The present invention has been made to solve the above problems of the prior art. An object thereof is to provide an oligofluorenylene compound that enables production of an organic light-emitting device that exhibits an extremely pure luminescent hue and has a light emission of high efficiency, high brightness, and long lifetime. Another object of the invention is to provide an oligofluorenylene compound with which there can be obtained an organic light-emitting device that can be not only easily manufactured but also produced at a relatively low cost.

According to the present invention, there is provided an oligofluorenylene compound represented by the following general formula (1).

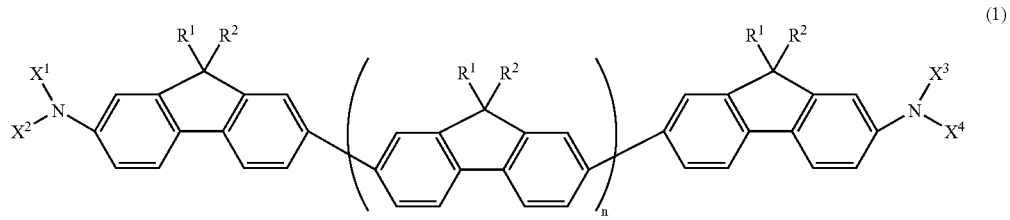

(wherein $X^1$ to $X^4$ are each a group selected from the group consisting of a substituted or unsubstituted alkyl group, aralkyl group, aryl group, and heterocyclic group, a substituted or unsubstituted alkenyl group, alkynyl group, amino group, alkoxy group, and sulfide group which have a connecting group comprising a substituted or unsubstituted arylene group or divalent heterocyclic group, and a substituted silyl group and carbonyl group which have a connecting group comprising a substituted or unsubstituted arylene group or divalent heterocyclic group, which may be the same or different, and $X^1$ and $X^2$, and $X^3$ and $X^4$ may be linked to each other to form a ring, wherein $R^1$ and $R^2$ are each a group selected from the group consisting of a hydrogen atom and a substituted or unsubstituted alkyl group, aralkyl group, and aryl group, $R^1$ and $R^2$ may be the same or different, and respective $R^1$'s and $R^2$'s on different fluorenylene rings may be the same or different, and wherein n is an integer of 1 to 20.)

BEST MODES FOR CARRYING OUT THE INVENTION

Figure 1:
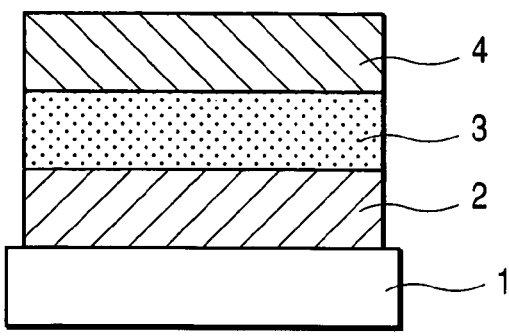
FIG. 1 is a sectional view showing an example of the organic light-emitting devices of the present invention.

The present invention will be explained in detail below.

First, an oligofluorenylene compound of the present invention will be explained.

The oligofluorenylene compound of the present invention is represented by the above general formula (1).

In the oligofluorenylene compound of the present invention, n in the above general formula (1) is preferably an integer from 1 to 4. That is, the compound is preferably one of a trifluorenylene compound, a tetrafluorenylene compound, a pentafluorenylene compound, and a hexafluorenylene compound.

Additionally, either of the substituents on each nitrogen atom is preferably a phenyl group having a substituent in at least the para or ortho position, which is represented by the following general formula (2).

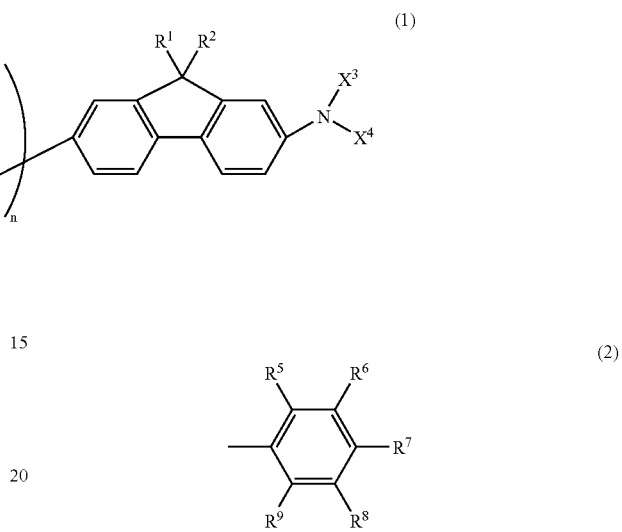

($R^5$ to $R^9$ each are a group selected from the group consisting of a hydrogen atom, halogen atom, cyano group, nitro group, substituted or unsubstituted alkyl group, aralkyl group, aryl group, heterocyclic group, alkenyl group, alkynyl group, amino group, alkoxy group, and sulfide group, and substituted silyl group and carbonyl group, which may be the same or different.)

Moreover, either of the substituents on each nitrogen atom is preferably an aromatic polycyclic condensed-ring group or a heterocyclic group.

Furthermore, it is preferred that one of the substituents on each nitrogen atom is a phenyl group that has at least one substituent in the para- or ortho-position and is represented by the above general formula (2), and the other substituent is an aromatic polycyclic condensed-ring group or a heterocyclic group.

Specific examples of the substituents in the above general formulae (1) and (2) are cited below.

The substituted or unsubstituted alkyl group may be either linear or cyclic. Examples thereof include a methyl group, ethyl group, n-propyl group, n-butyl group, n-hexyl group, n-decyl group, iso-propyl group, iso-butyl group, tert-butyl group, tert-octyl group, trifluoromethyl group, cyclohexyl group, cyclohexylmethyl group, etc., although of course they are not limited to the above.

Examples of substituted or unsubstituted aralkyl groups include a benzyl group, phenethyl group, etc., although of course they are not limited to those.

Examples of substituted or unsubstituted aryl groups include a phenyl group, 4-methylphenyl group, 4-methoxyphenyl group, 4-ethylphenyl group, 4-fluorophenyl group, 3,5-dimethylphenyl group, ditolylaminopheynyl group, biphenyl group, terphenyl group, naphthyl group, anthracenyl group, phenanthrenyl group, pyrenyl group, tetracenyl group, pentacenyl group, fluorenyl group, triphenylenyl group, perylenyl group, etc., although of course they are not limited to those.

Examples of substituted or unsubstituted heterocyclic groups include a pyrrolyl group, pyridyl group, bipyridyl group, methylpyridyl group, terpyrrolyl group, thienyl group, terthienyl group, propylthienyl group, furil group, quinolyl group, carbazolyl group, oxazolyl group, oxadiazolyl group, thiazolyl group, thiadiazolyl group, etc., although of course they are not limited to those.

Examples of substituted or unsubstituted arylene groups include a phenylene group, biphenylene group, 2,3,5,6-tetrafluorophenylene group, 2,5-dimethylphenylene group, naphthylene group, anthracenylene group, phenanthrenylene group, tetracenylene group, pentacenylene group, perylenylene group, etc., although of course they are not limited to those.

Examples of substituted or unsubstituted divalent heterocyclic groups include a furanylene group, pyrrolylene group, pyridinylene group, terpyridinylene group, thiophenylene group, terthiophenylene group, oxazolylene group, thiazolylene group, carbazolylene group, etc., although of course they are not limited to those.

Examples of substituted or unsubstituted alkenyl groups include a vinyl group, allyl group (2-propenyl group), 1-propenyl group, iso-propenyl group, 2-butenyl group, etc., although of course they are not limited to those.

Examples of substituted or unsubstituted alkynyl groups include an acetylenyl group, phenylacetylenyl group, 1-propynyl group, etc., although of course they are not limited to those.

Examples of substituted or unsubstituted amino groups include an amino group, methylamino group, ethylamino group, dimethylamino group, diethylamino group, methylethylamino group, benzylamino group, methylbenzylamino group, dibenzylamino group, anilino group, diphenylamino group, phenyltolylamino group, ditolylamino group, dianisolylamino group, etc., although of course they are not limited to those.

Examples of substituted or unsubstituted alkoxy groups include a methoxy group, ethoxy group, propoxy group, 2-ethyl-octyloxy group, phenoxy group, 4-butylphenoxy group, benzyloxy group, etc., although of course they are not limited to those.

Examples of substituted or unsubstituted sulfide groups include a methylsulfide group, ethylsulfide group, phenylsulfide group, 4-methylphenylsulfide group, etc., although of course they are not limited to those.

Examples of substituted carbonyl groups include an acetyl group, propionyl group, isobutyryl group, methacryloyl group, benzoyl group, naphthoyl group, anthroyl group, toluoyl group, etc., although of course they are not limited to those.

Examples of substituents that the above substituted groups may have include: alkyl groups and aralkyl groups such as a methyl group, ethyl group, n-propyl group, iso-propyl group, tert-butyl group, octyl group, benzyl group, and phenethyl group; alkoxy groups such as a methoxy group, ethoxy group, propoxy group, 2-ethyl-octyloxy group, phenoxy group, 4-butylphenoxy group, and benzyloxy group; aryl groups such as a phenyl group, 4-methylphenyl group, 4-ethylphenyl group, 3-chlorophenyl group, 3,5-dimethylphenyl group, triphenylamino group, biphenyl group, terphenyl group, naphthyl group, anthryl group, phenanthryl group, and pyrenyl group; heterocyclic groups such as a pyridyl group, bipyridyl group, methylpyridyl group, thienyl group, terthienyl group, propylthienyl group, furil group, quinolyl group, carbazolyl group, and N-ethylcarbazolyl group; halogen groups; cyano group; and nitro group, although of course they are not limited to those.

Next, typical examples of the fluorenylene compounds represented by the general formula (1) are shown below. However, the compounds of the present invention are not limited to these compounds.

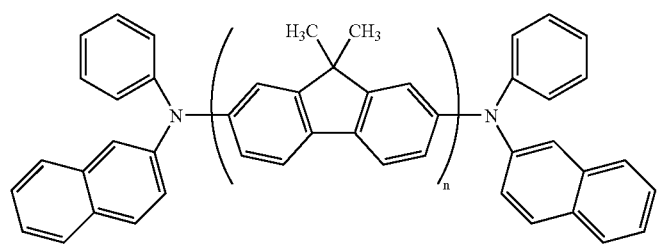

a: n = 3, b: n = 4, c: n = 5, d: n = 6

1

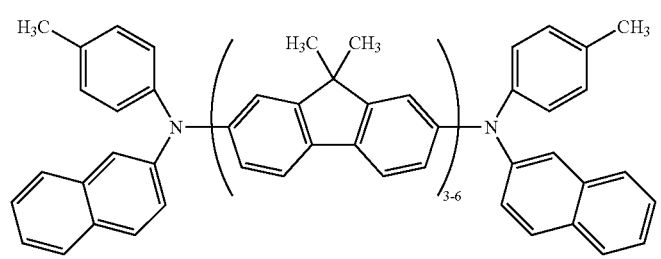

2a-d

-continued
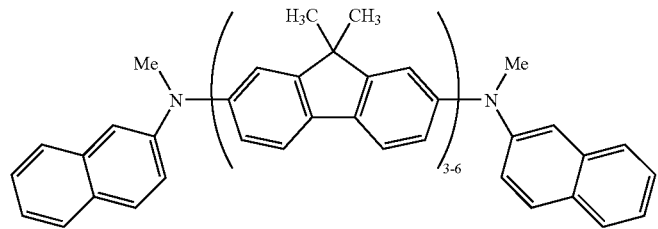
3a-d
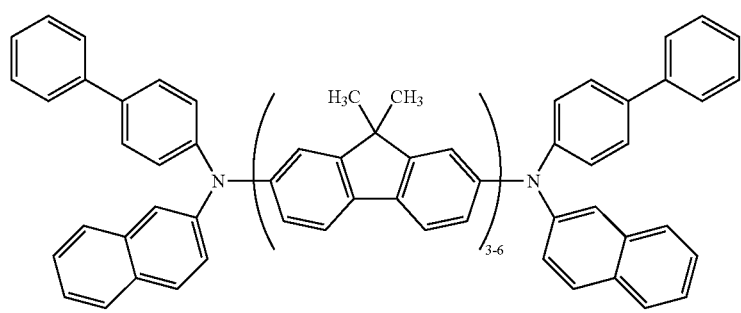
4a-d
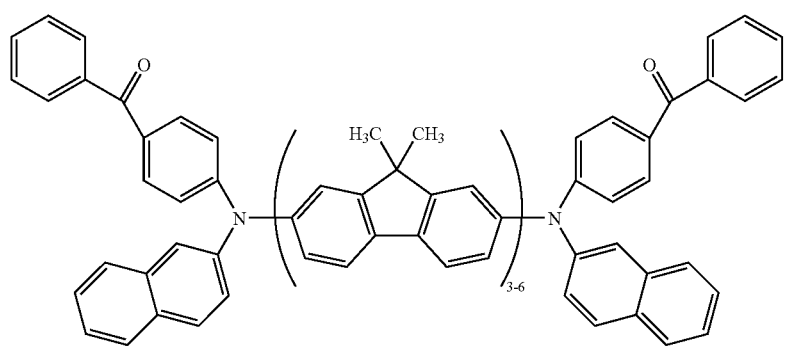
5a-d
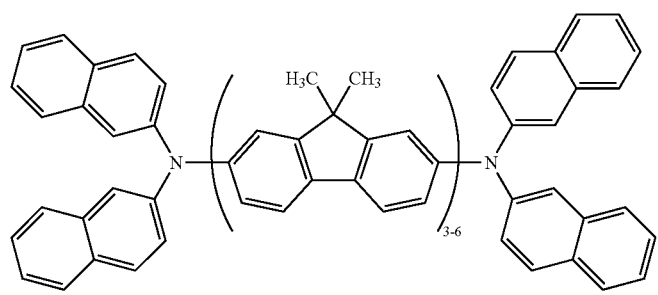
6a-d
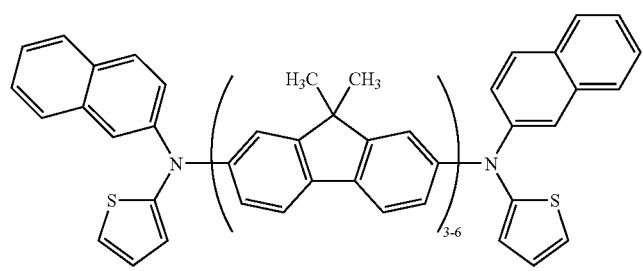
7a-d -continued
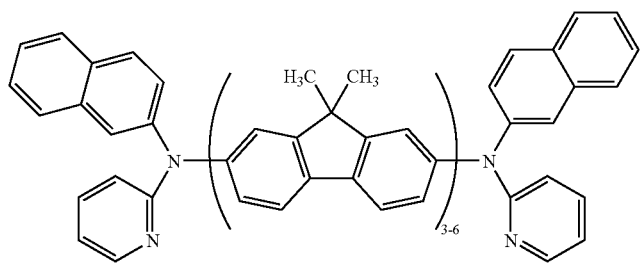
8a-d
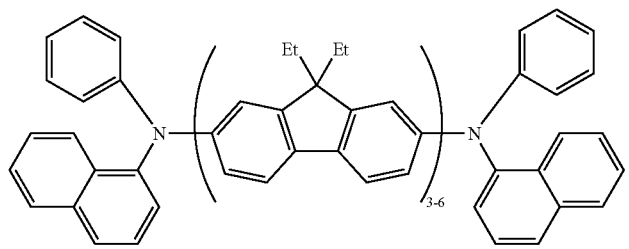
9a-d
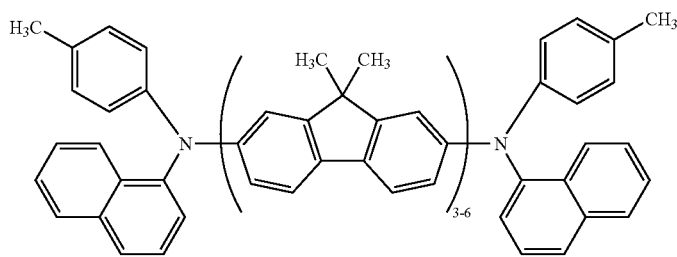
10a-d
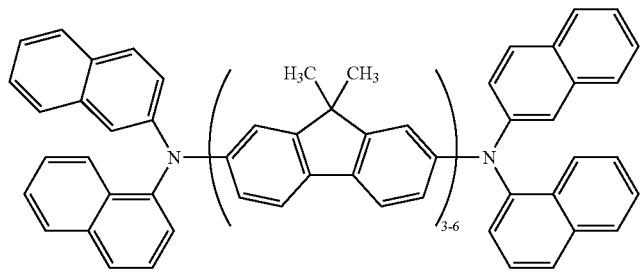
11a-d
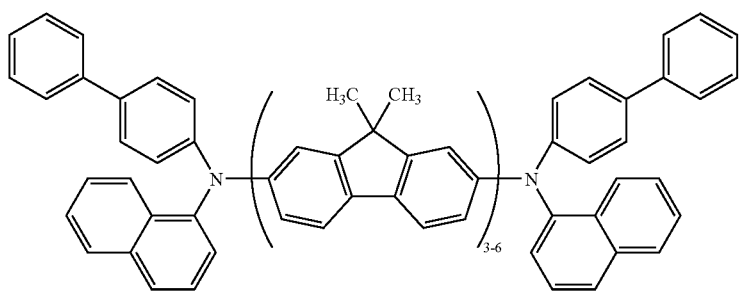
12a-d -continued
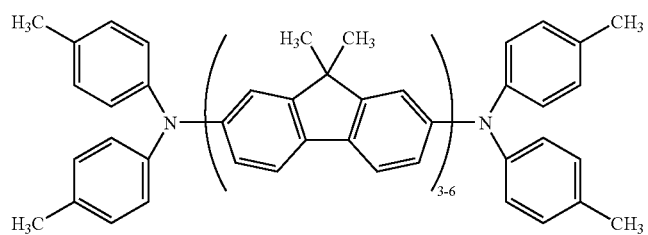
13a-d
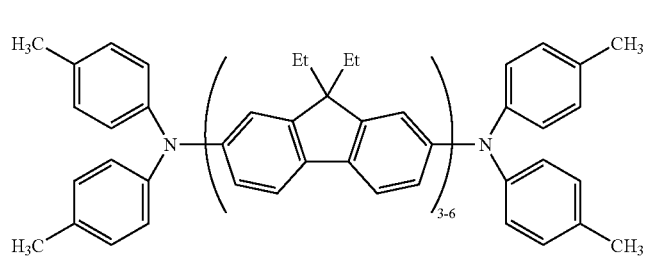
14a-d
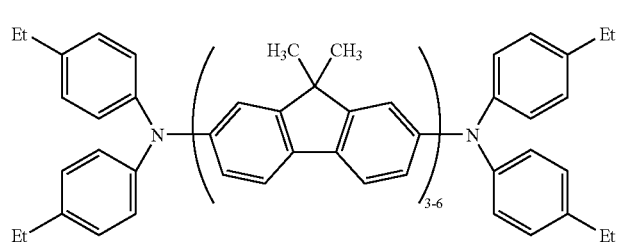
15a-d
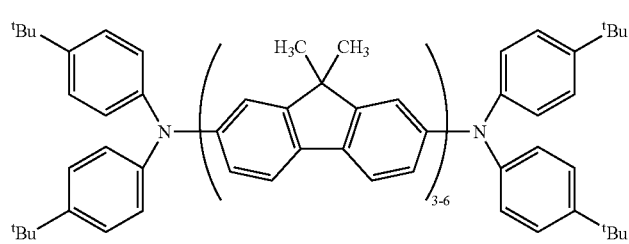
16a-d
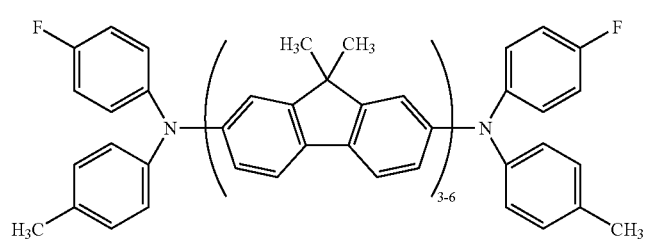
17a-d
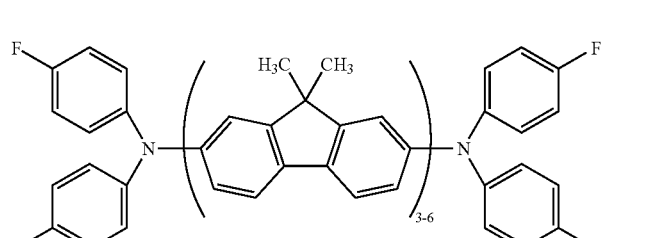
18a-d -continued
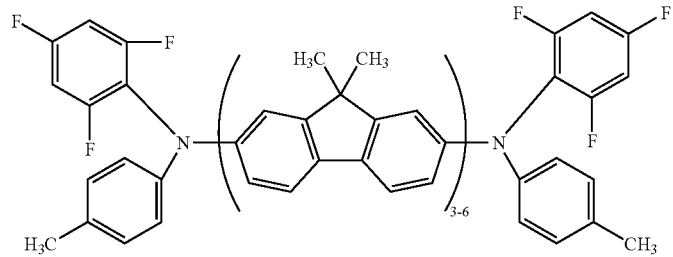
19a-d
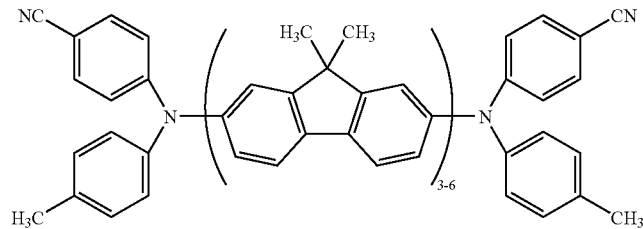
20a-d
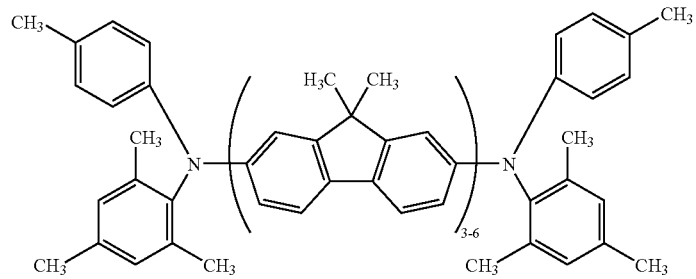
21a-d
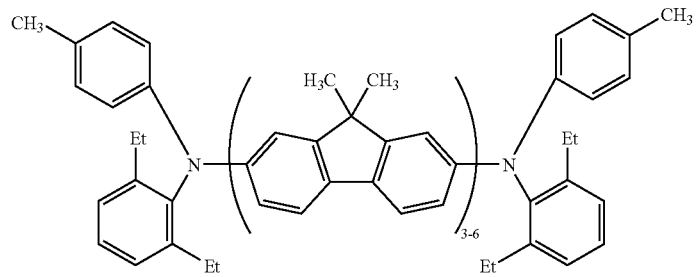
22a-d
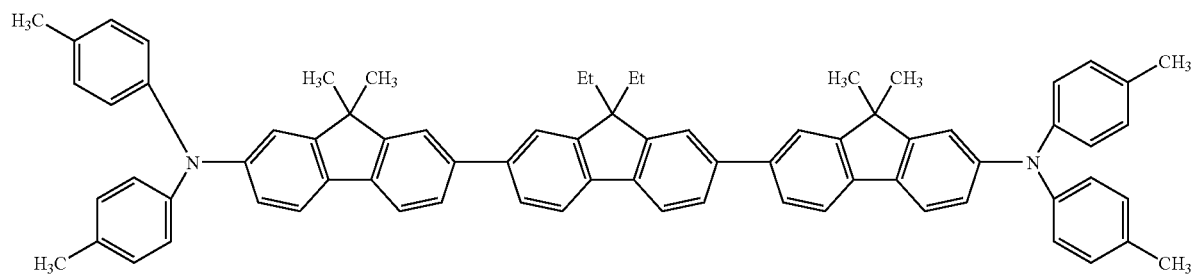
23

-continued
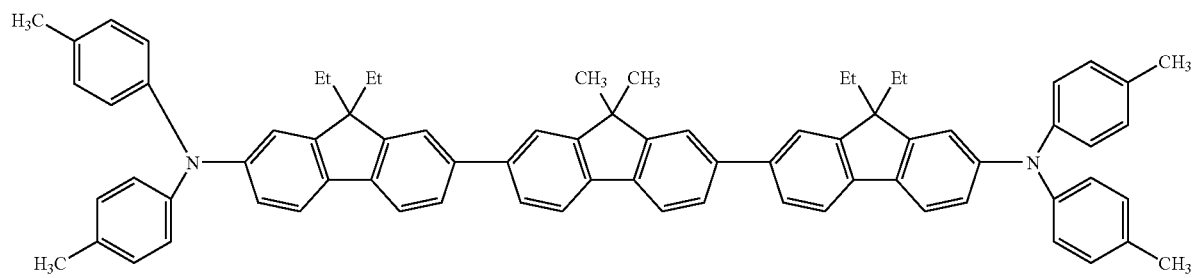
24
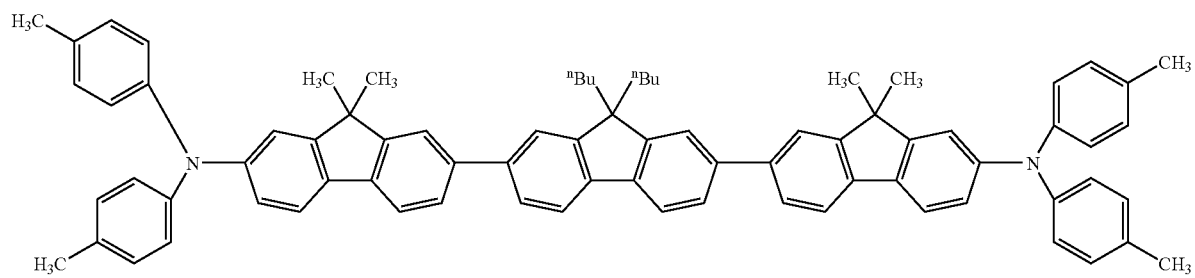
25
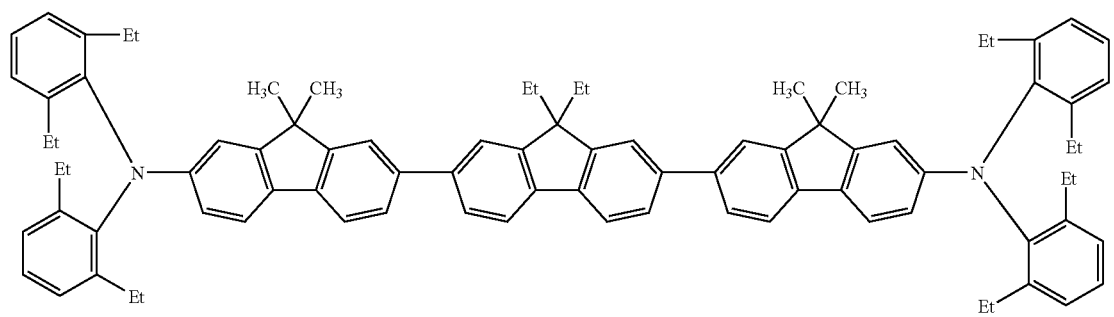
26
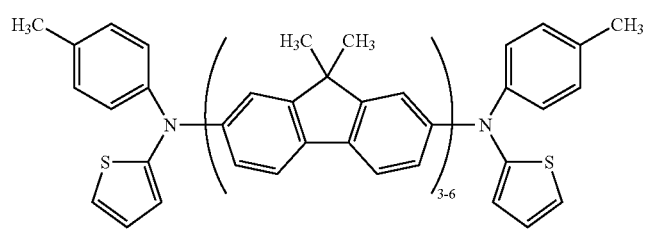
27a-d
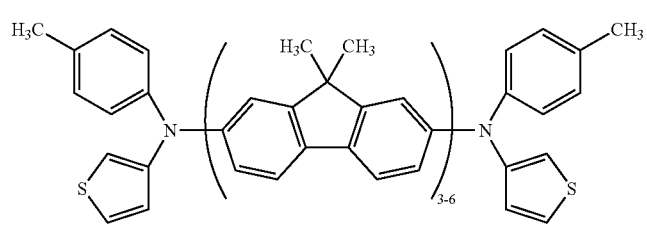
28a-d -continued
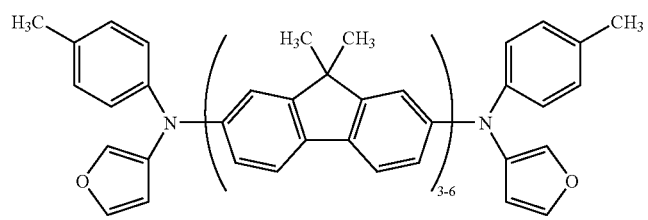
29a-d
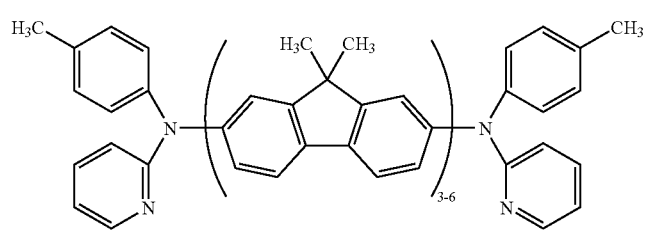
30a-d
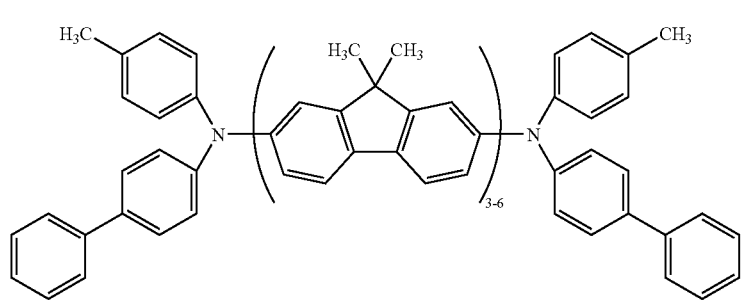
31a-d
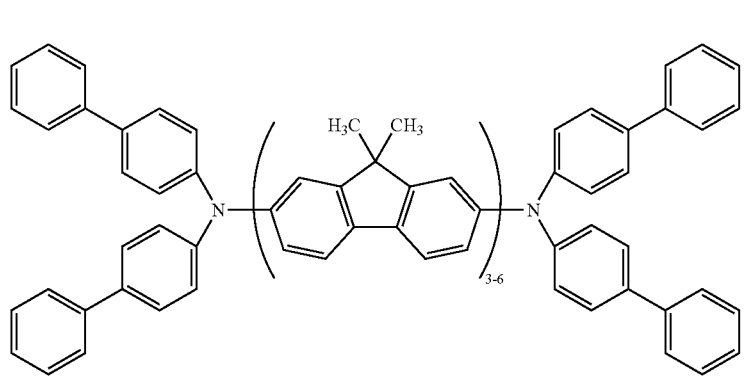
32a-d
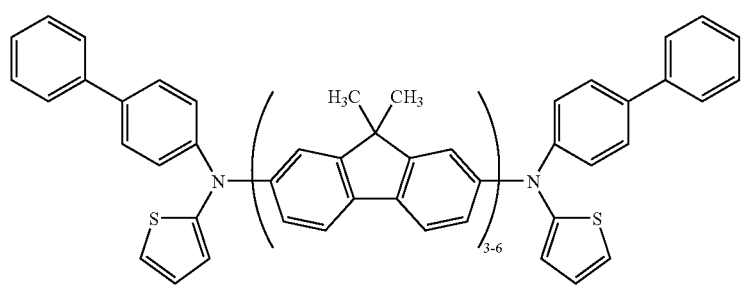
33a-d

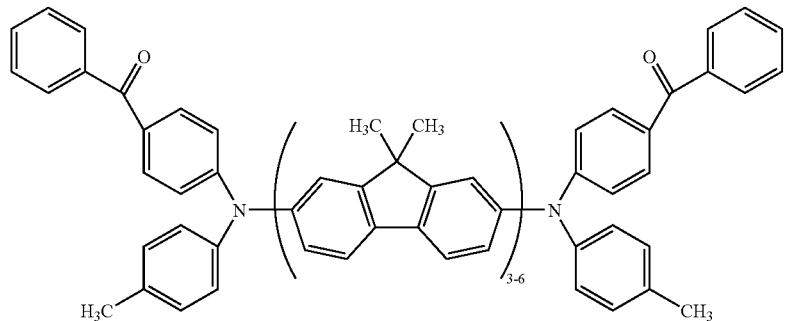
34a–d
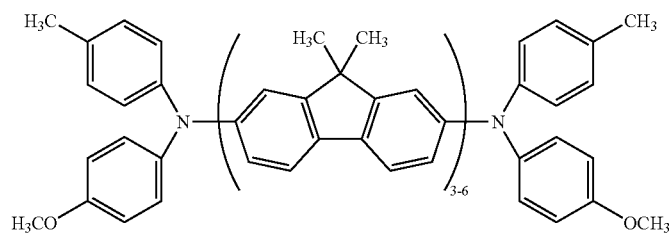
35a–d
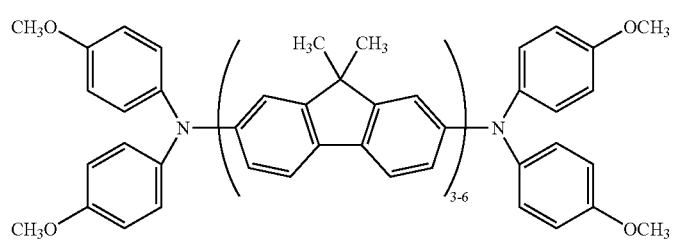
36a–d
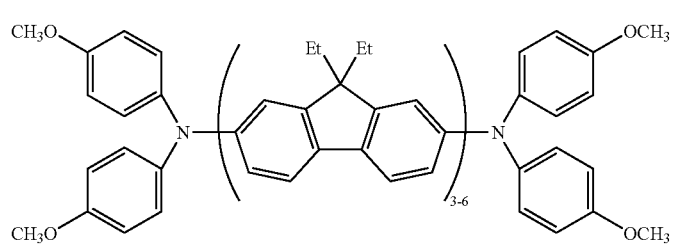
37a–d
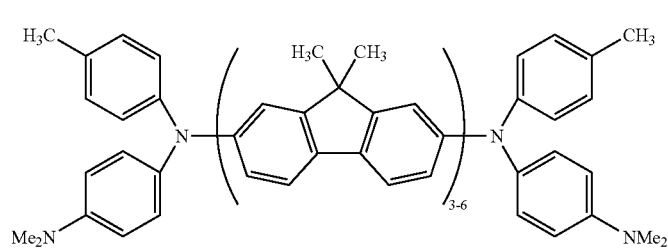
38a–d -continued
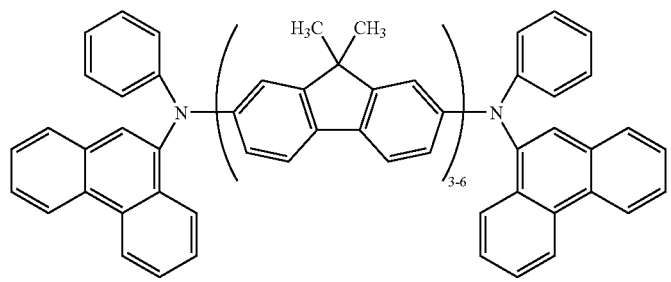
39a-d
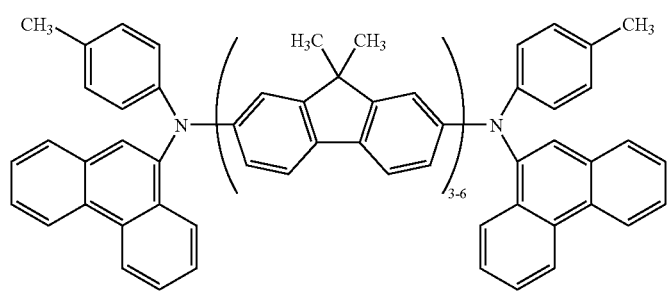
40a-d
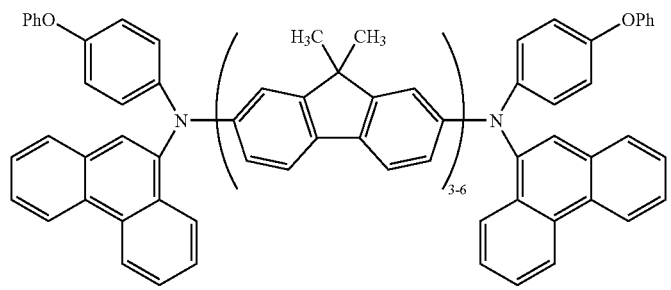
41a-d
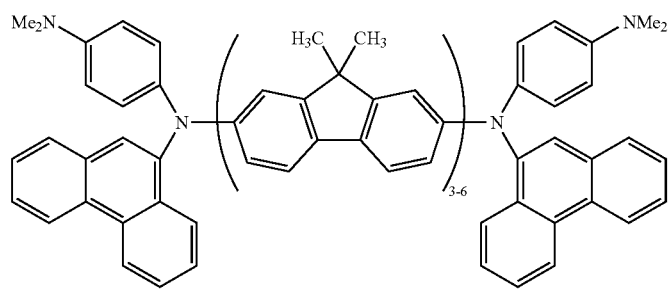
42a-d
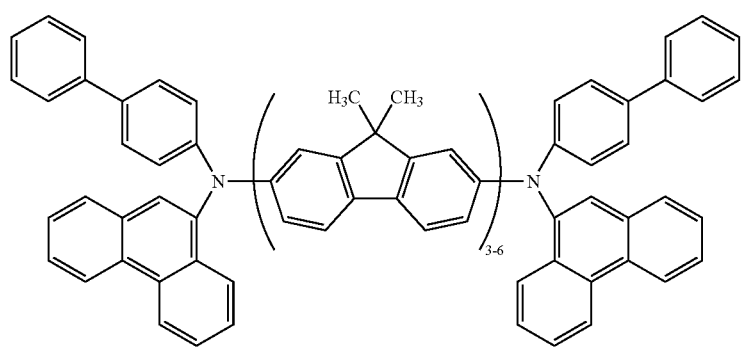
43a-d -continued
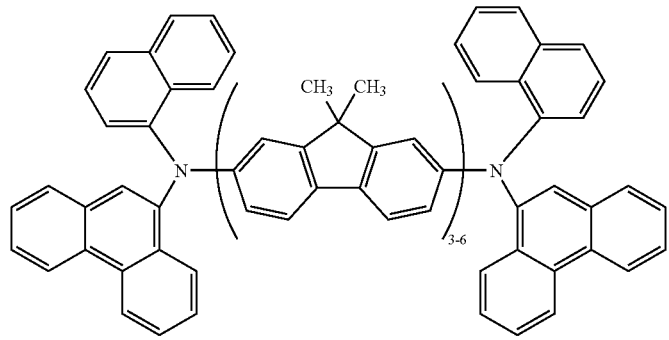
44a-d
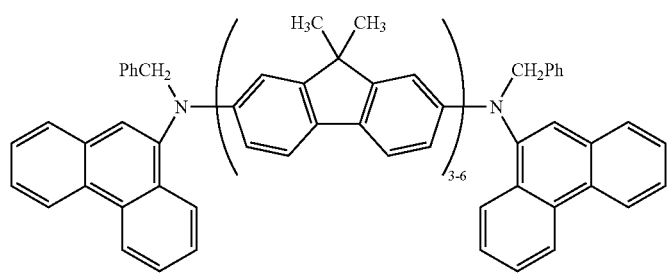
45a-d
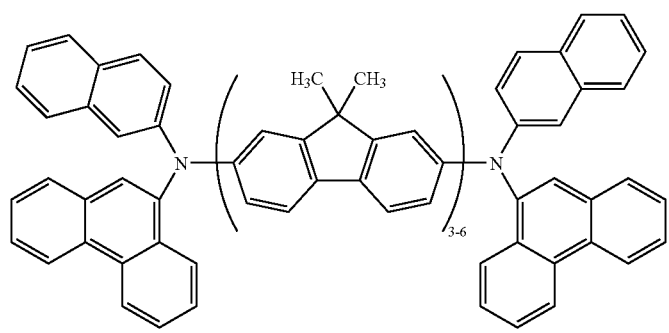
46a-d
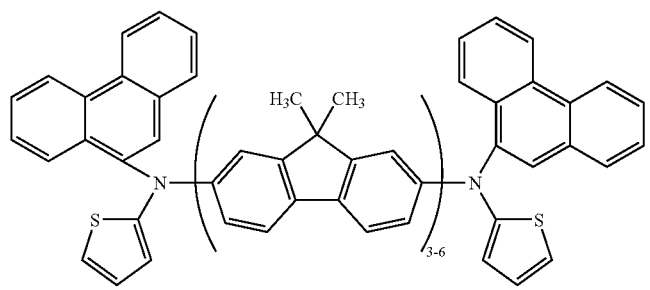
47a-d
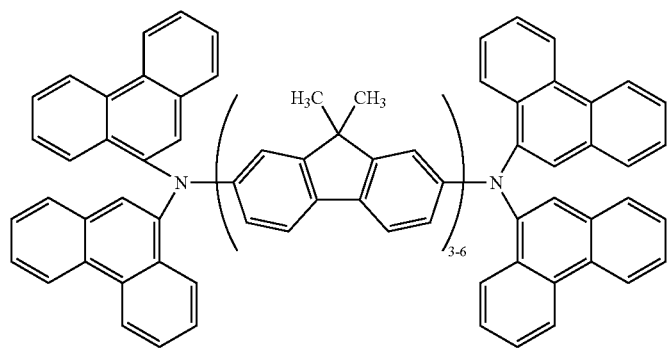
48a-d -continued
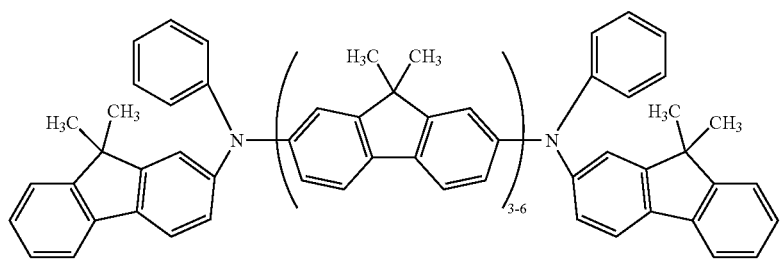
49a-d
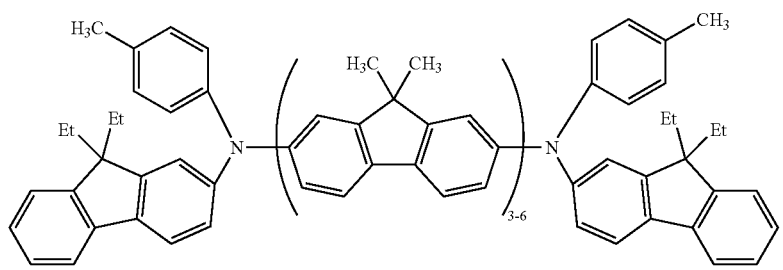
50a-d
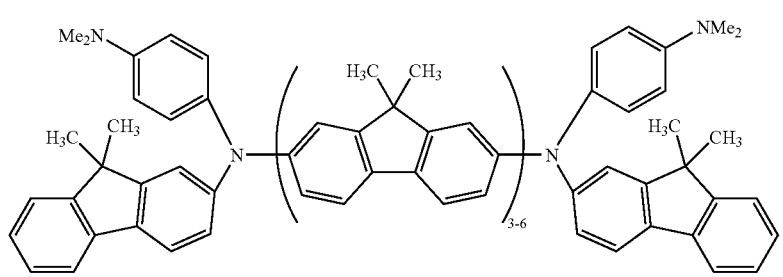
51a-d
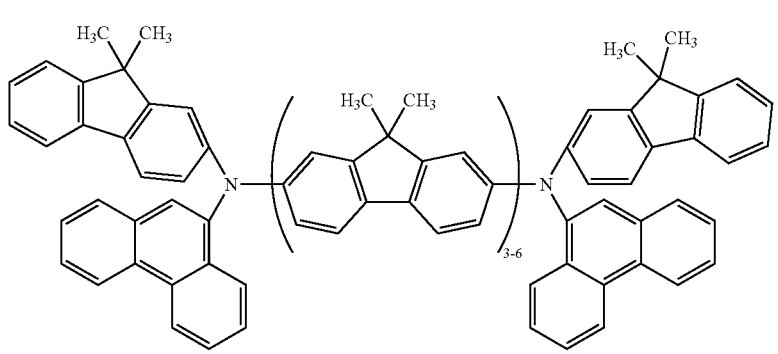
52a-d
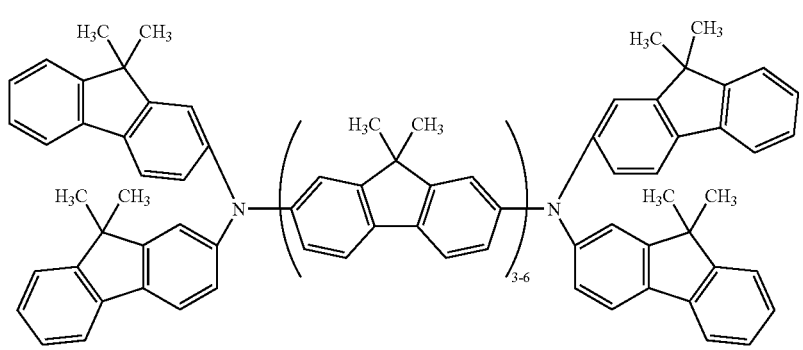
53a-d -continued
54a-d
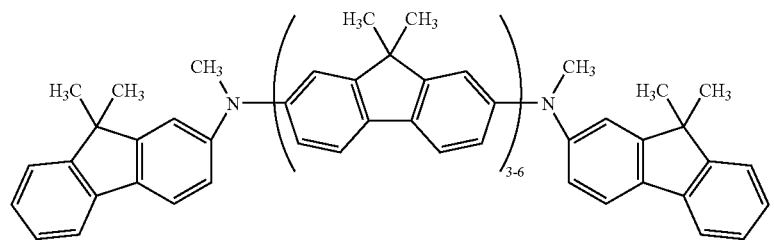
55a-d
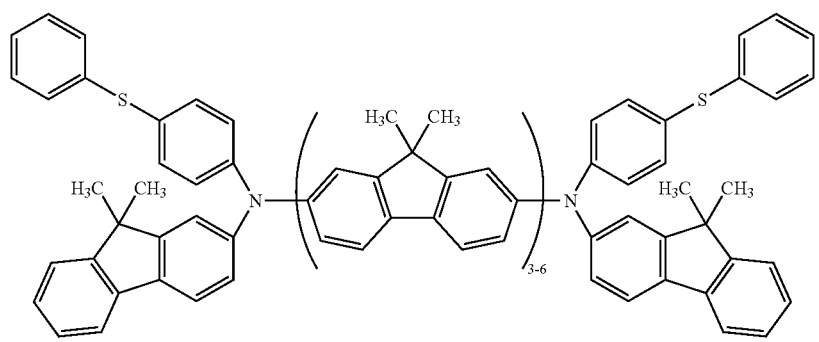
56a-d
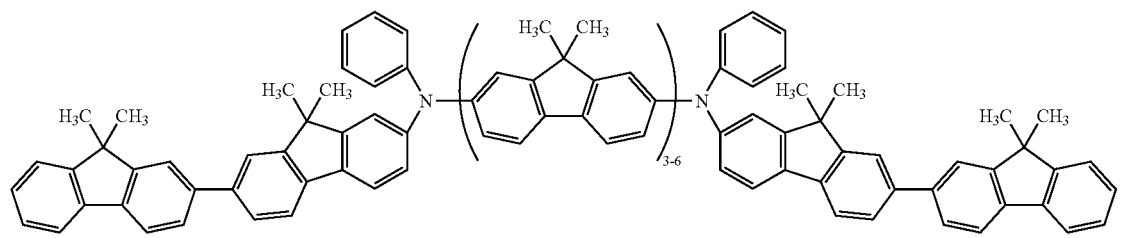
57a-d
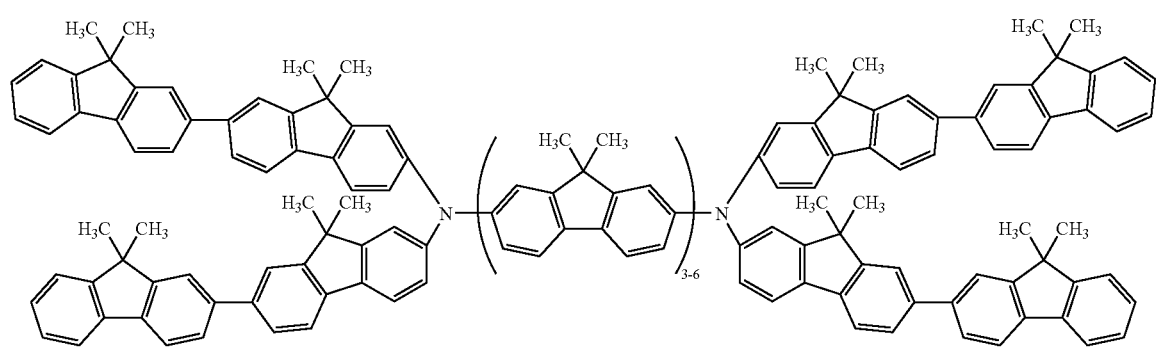
58a-d
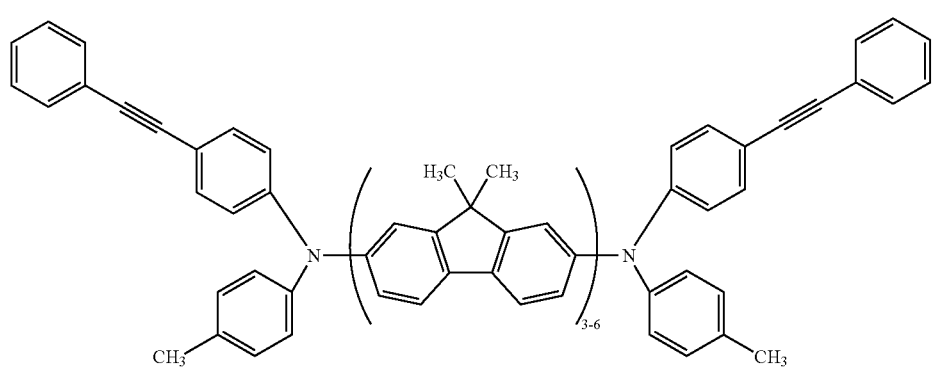

-continued
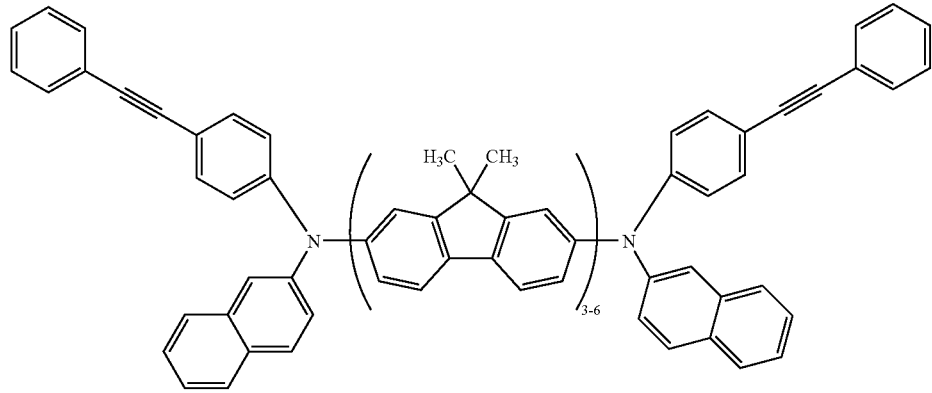
59a-d
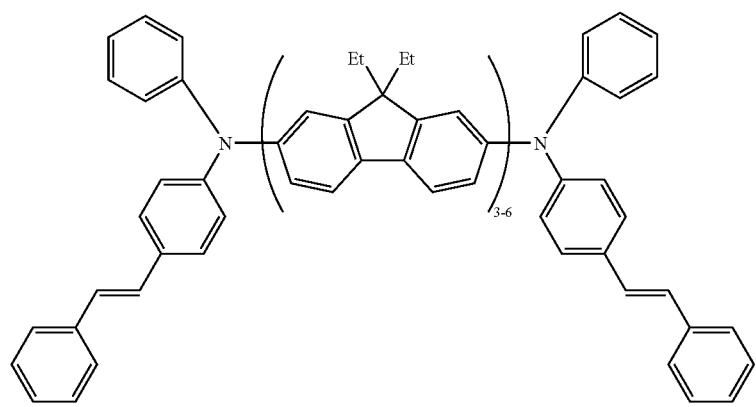
60a-d
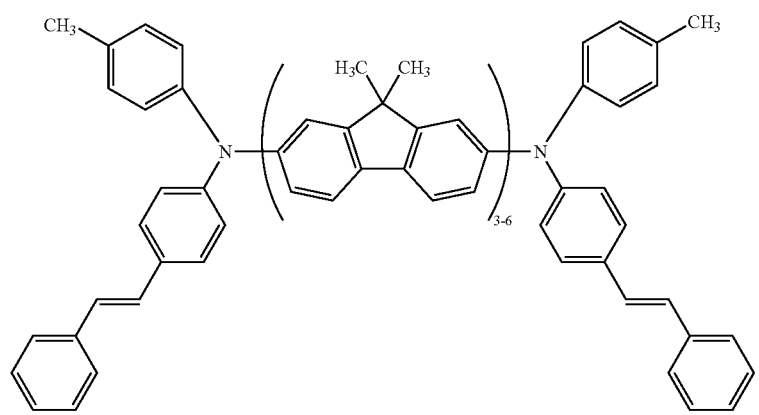
61a-d

-continued
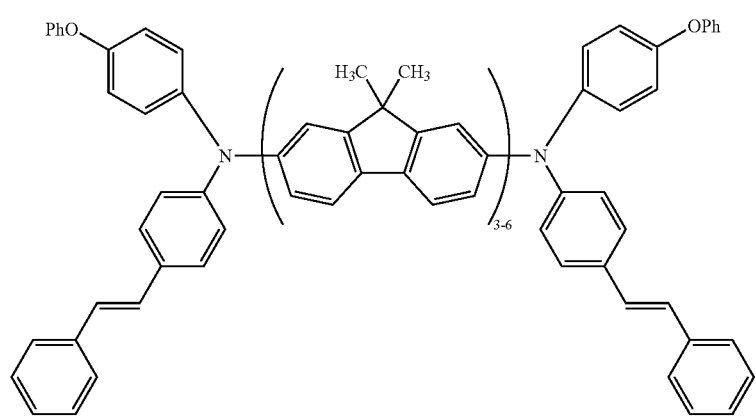
62a-d
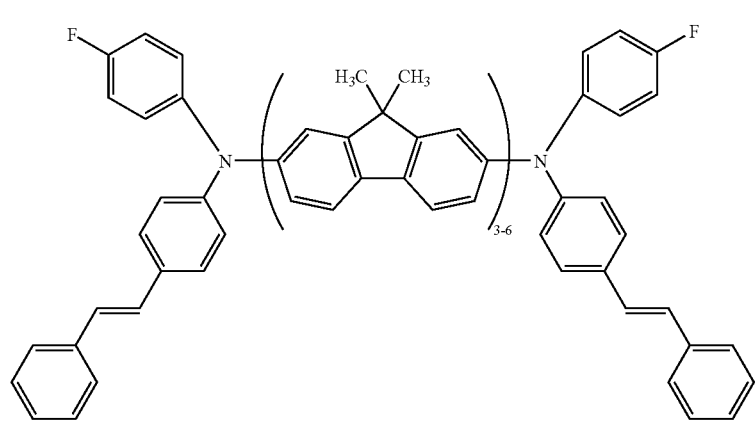
63a-d
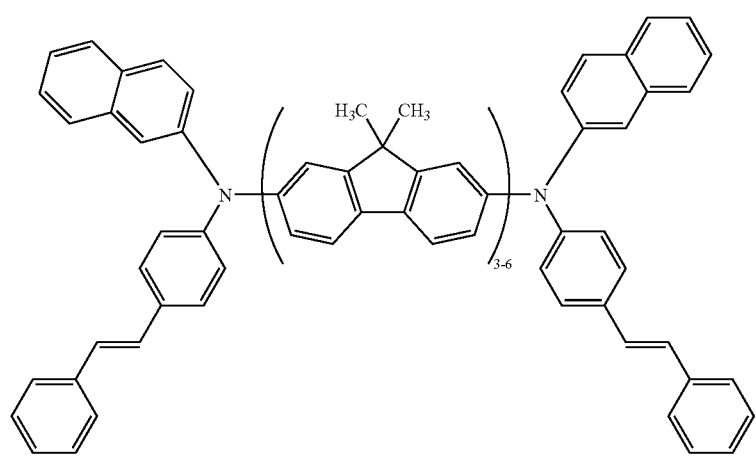
64a-d

-continued
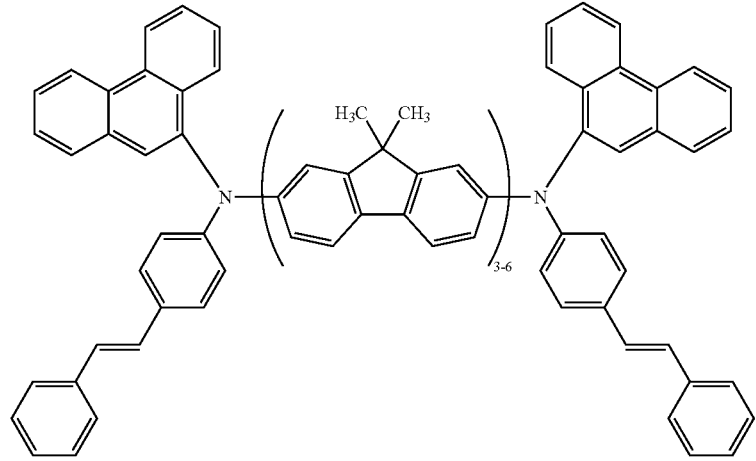
65a-d
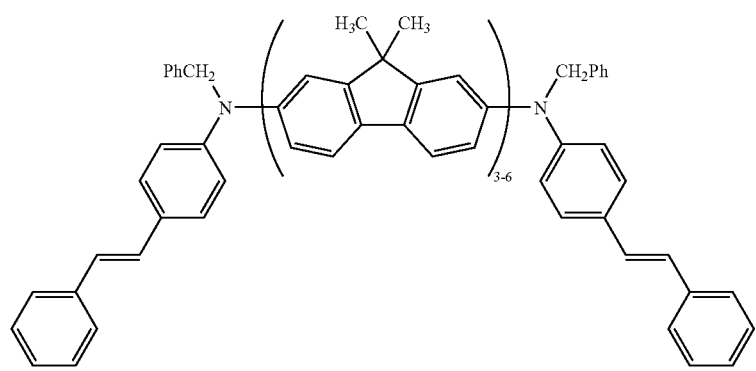
66a-d
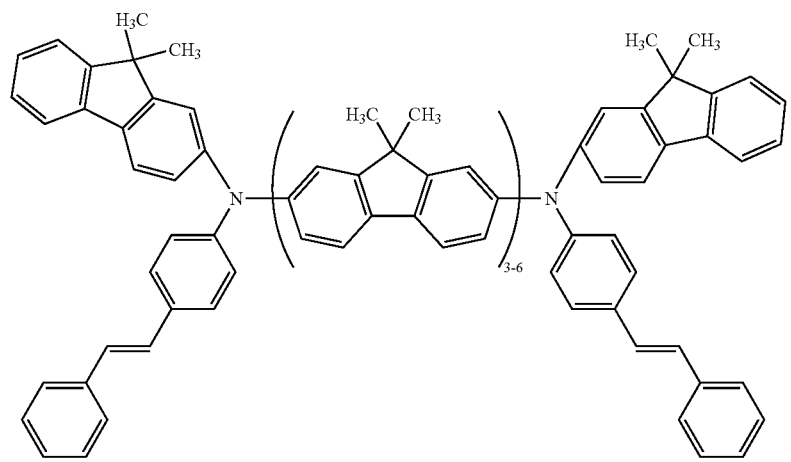
67a-d

-continued
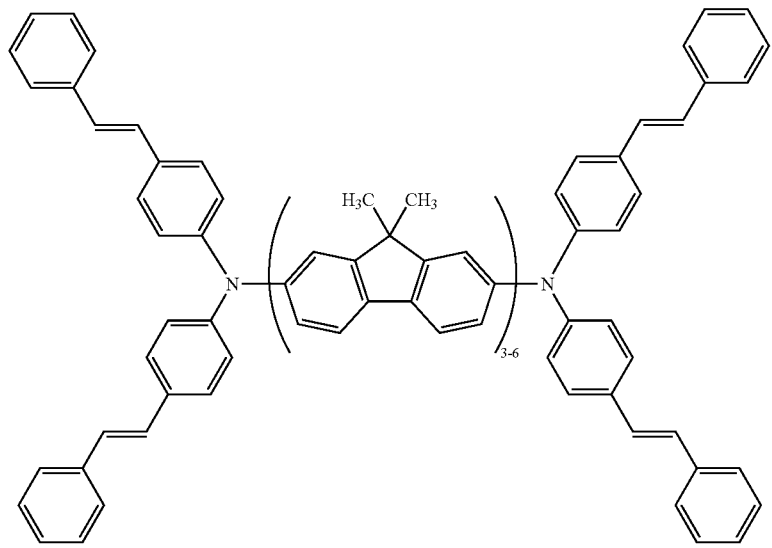
68a-d
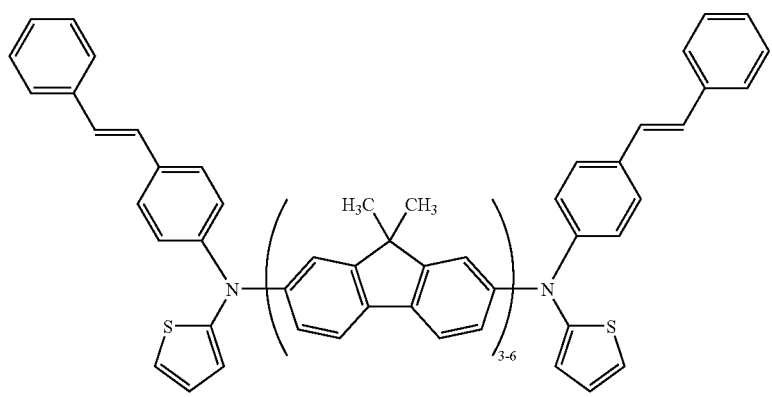
69a-d
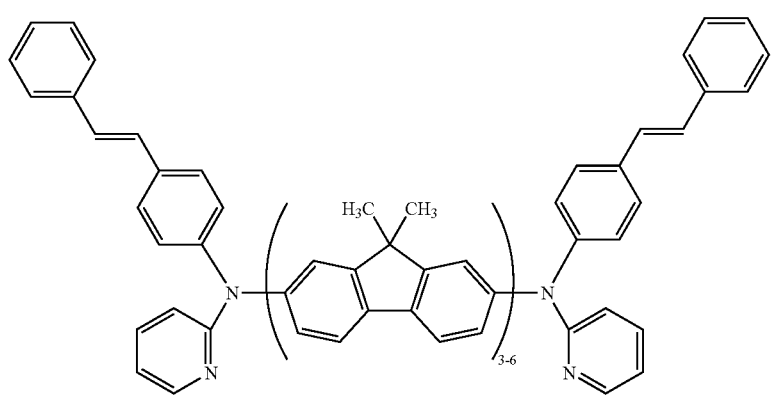
70a-d

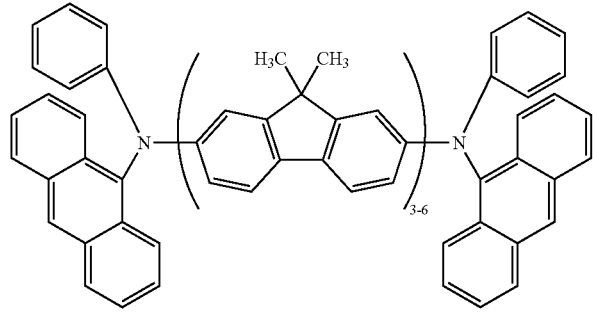
71a-d
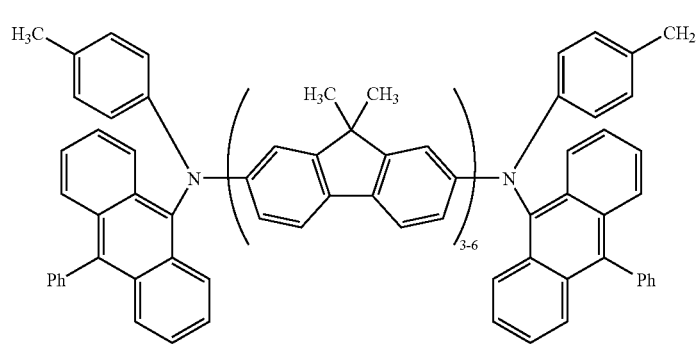
72a-d
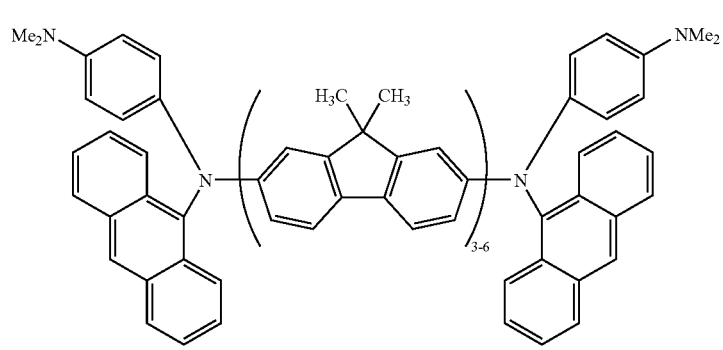
73a-d
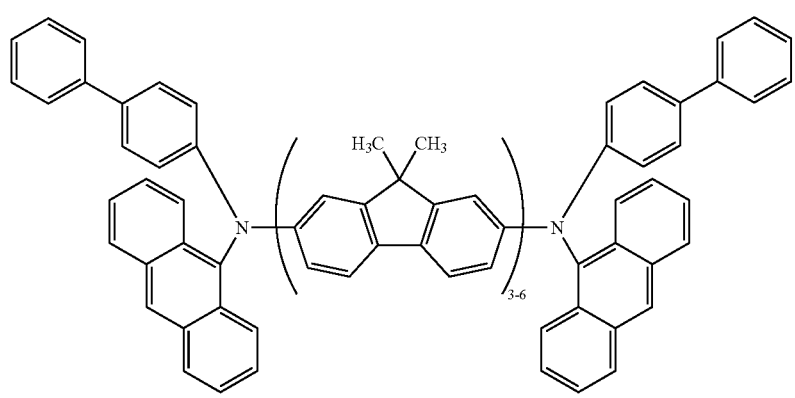
74a-d

-continued
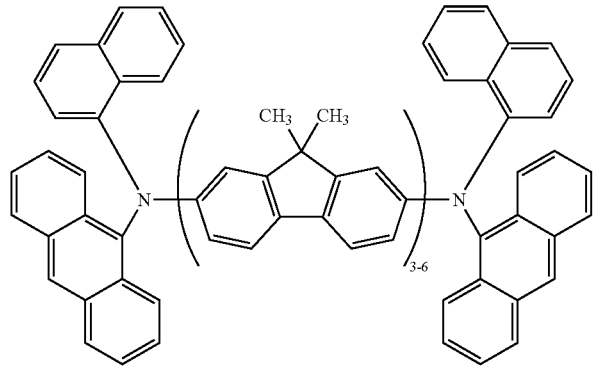
75a-d
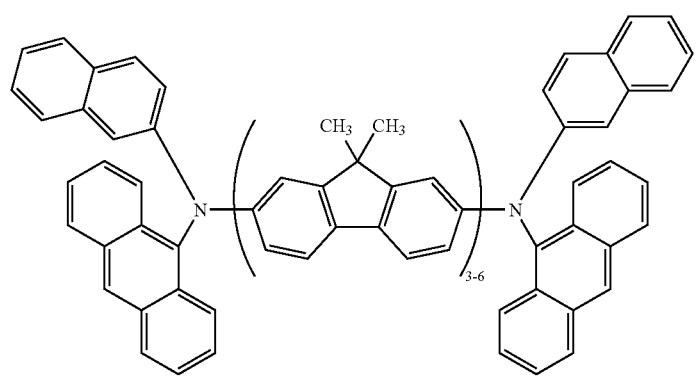
76a-d
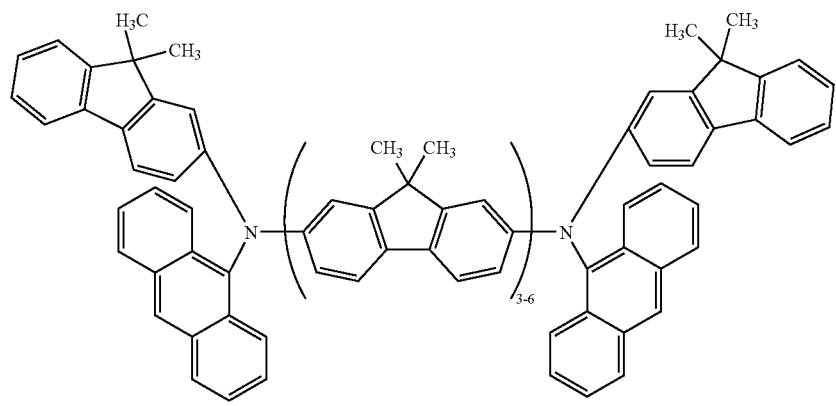
77a-d

-continued
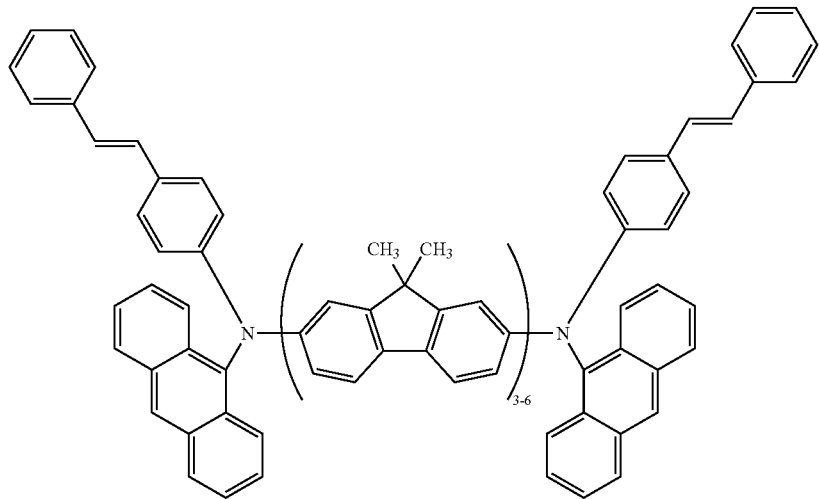
78a-d
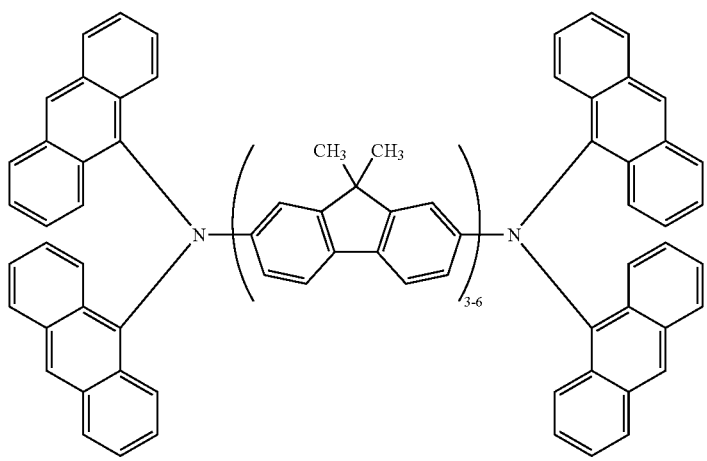
79a-d
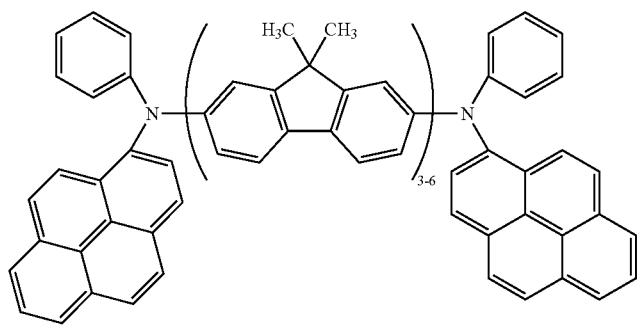
80a-d

-continued
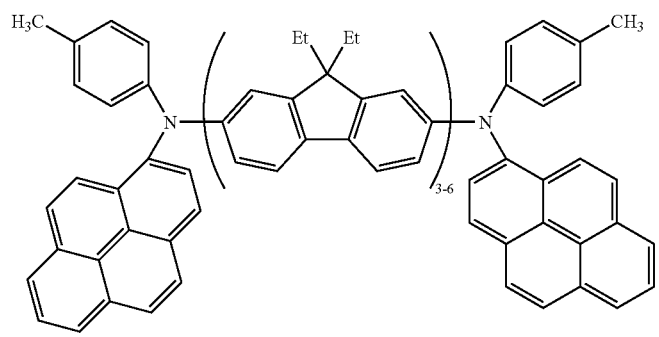
81a-d
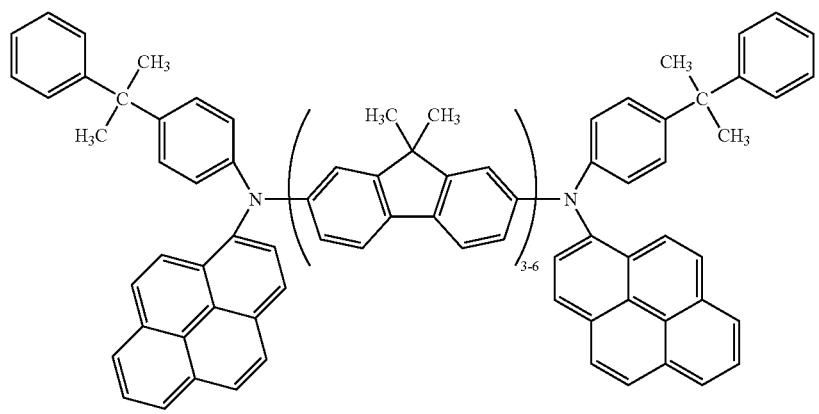
82a-d
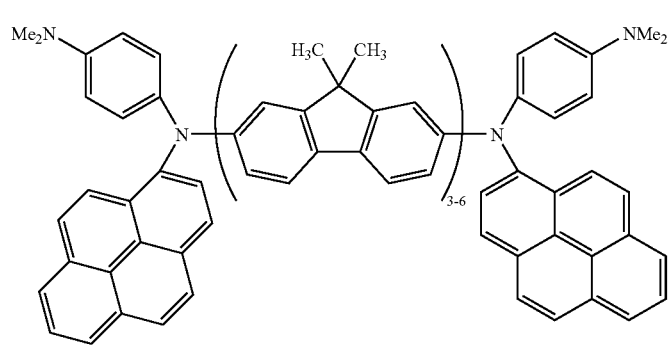
83a-d
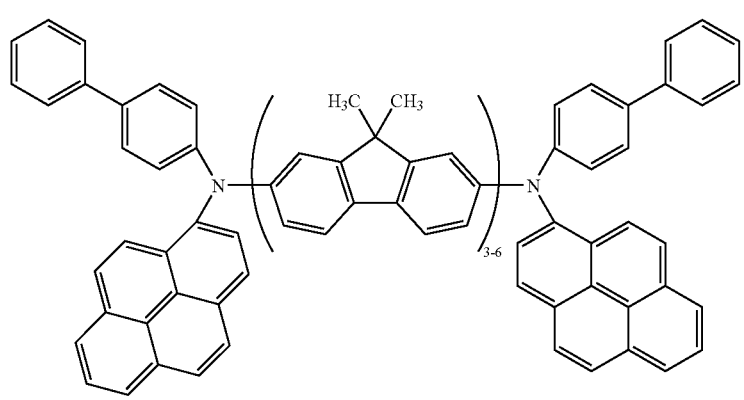
84a-d

-continued
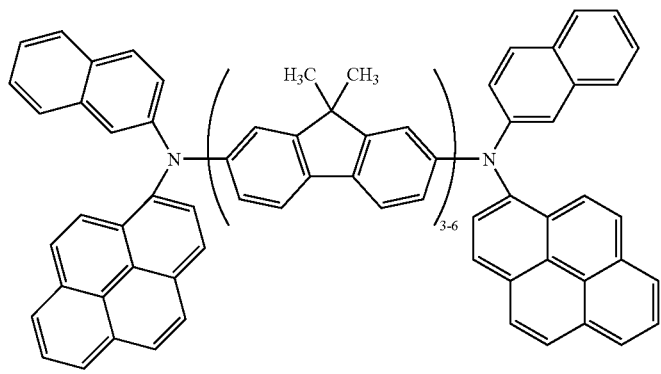
85a-d
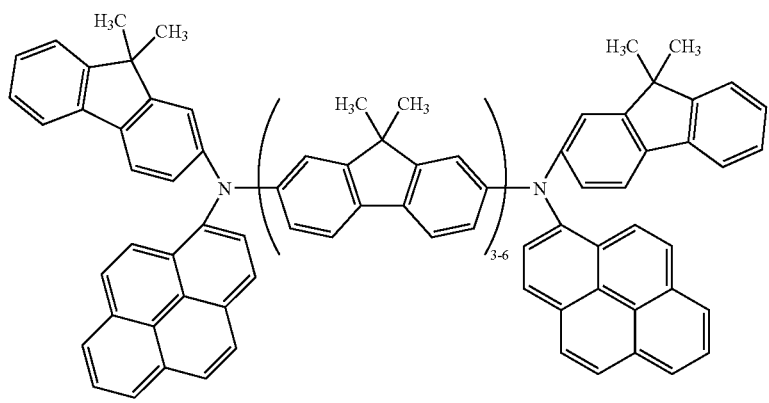
86a-d
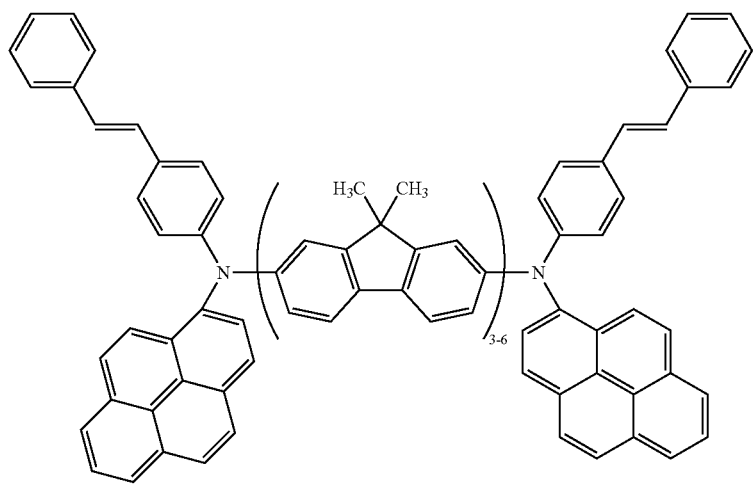
87a-d

-continued
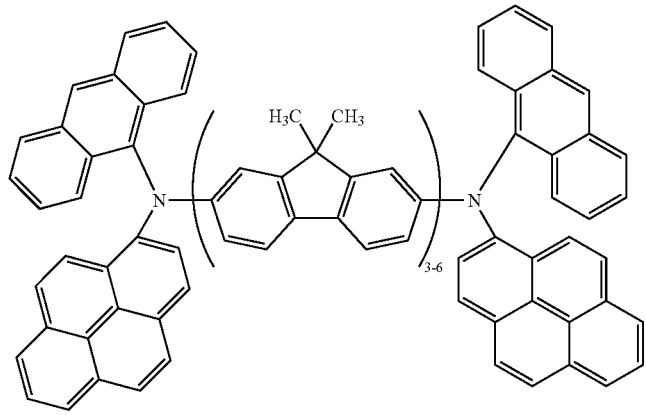
88a-d
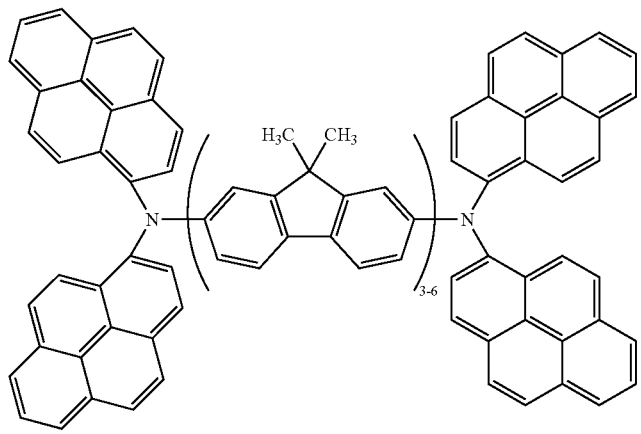
89a-d
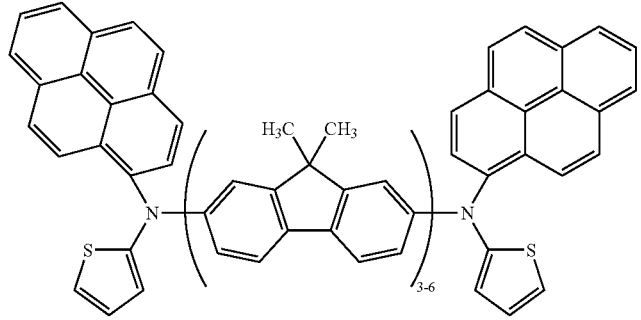
90a-d
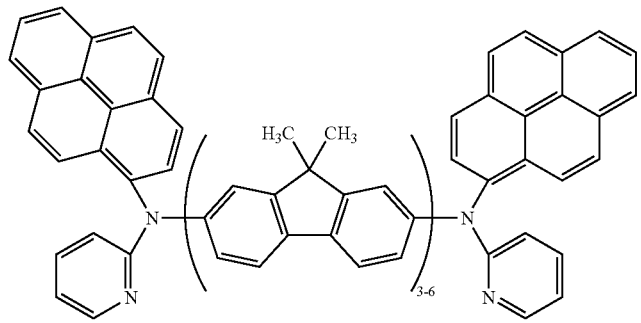
91a-d

-continued
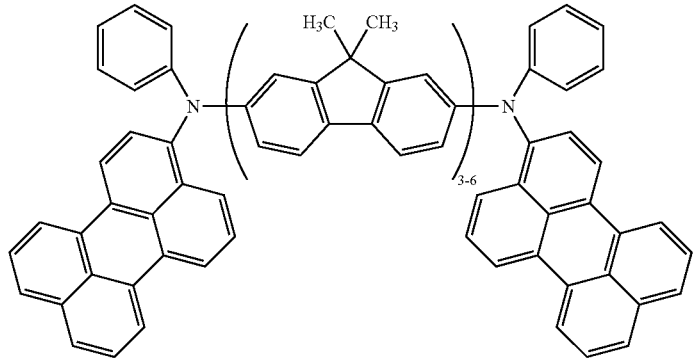
92a-d
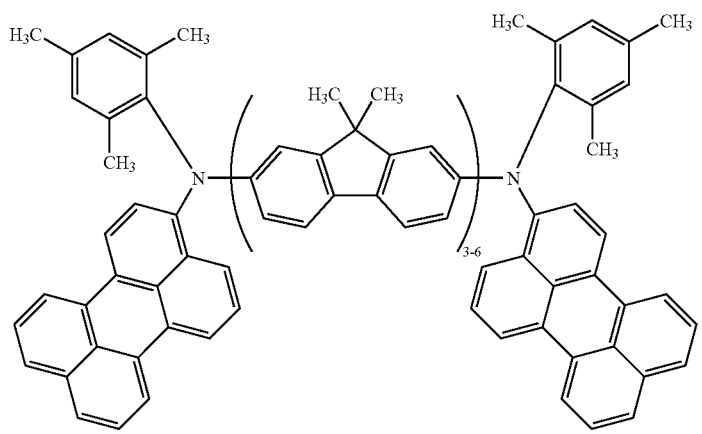
93a-d
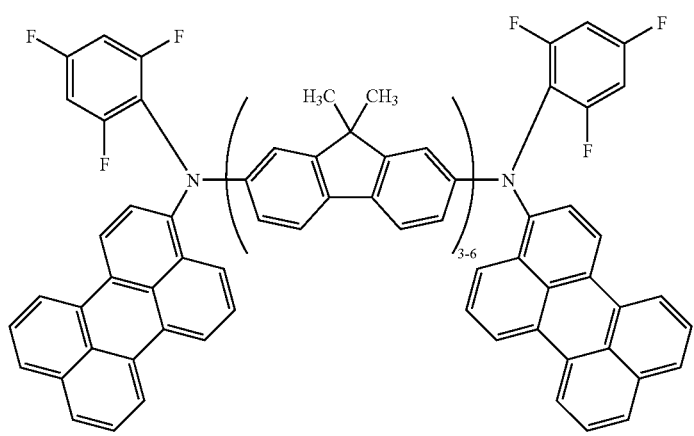
94a-d

-continued
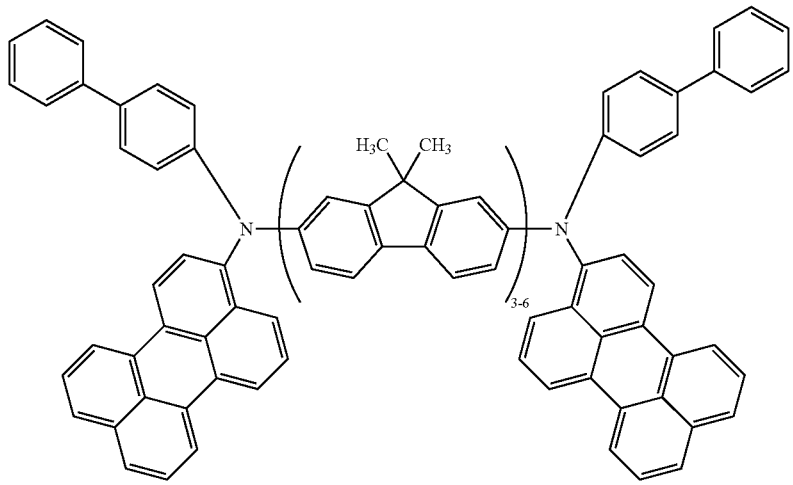
95a-d
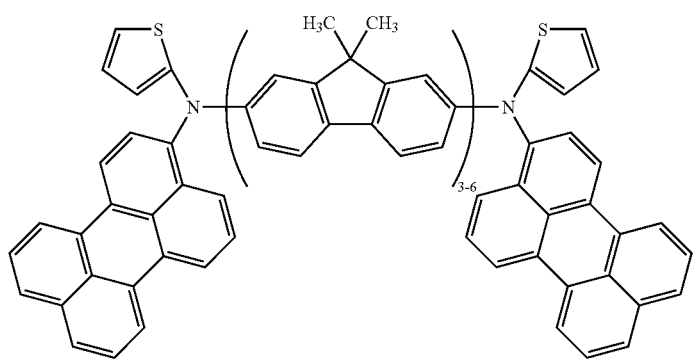
96a-d
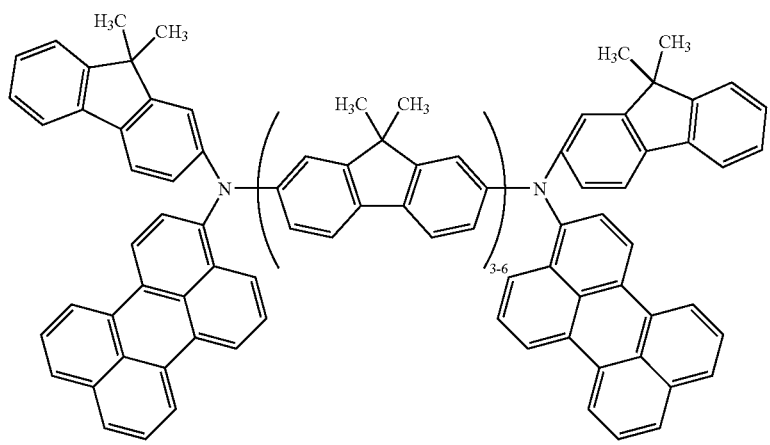
97a-d

-continued
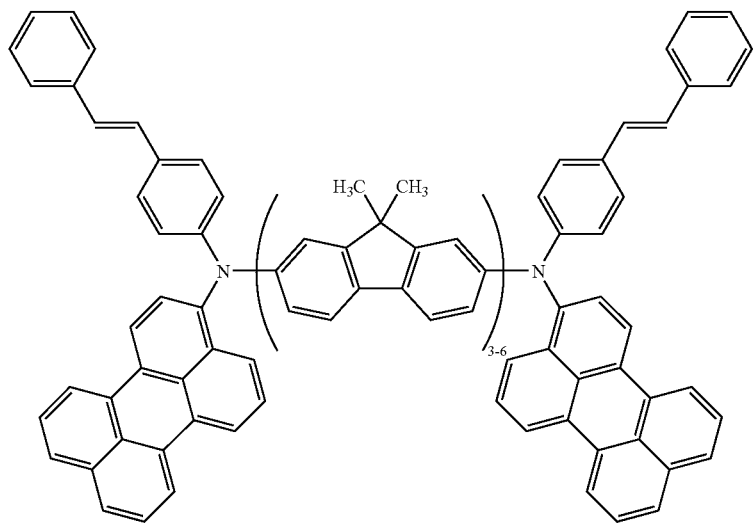
98a-d
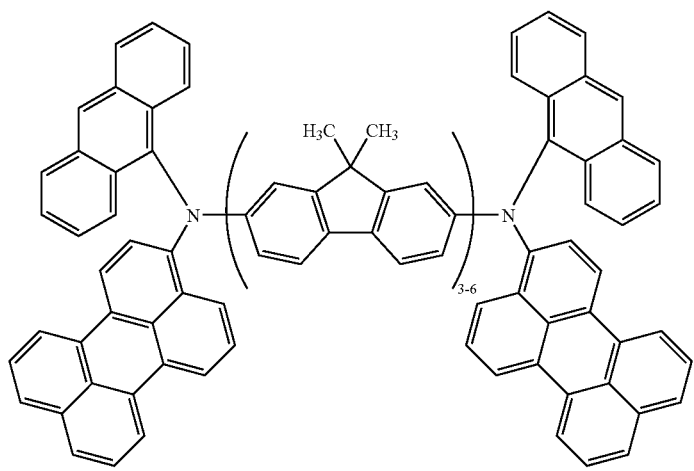
99a-d
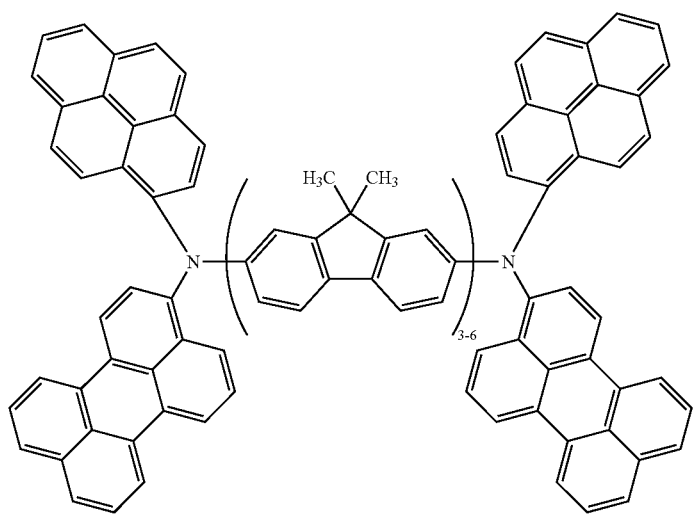
100a-d

-continued
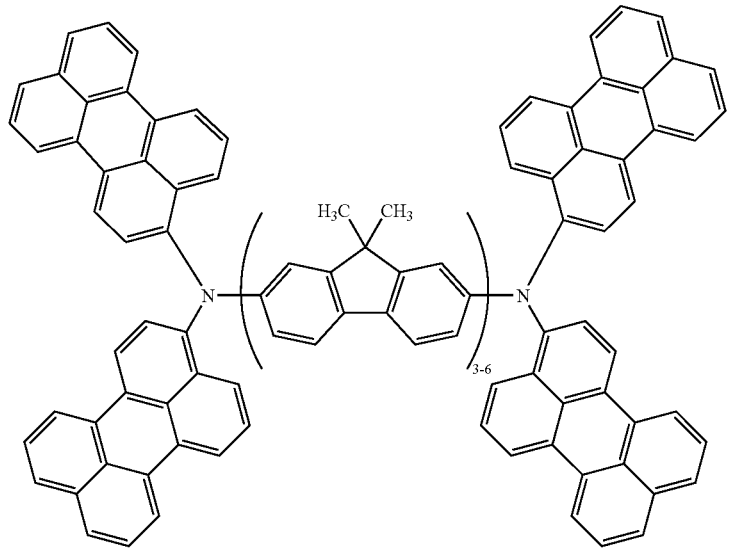
101a-d
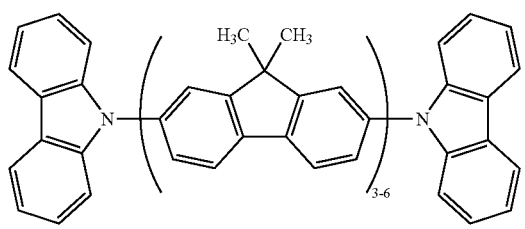
102a-d
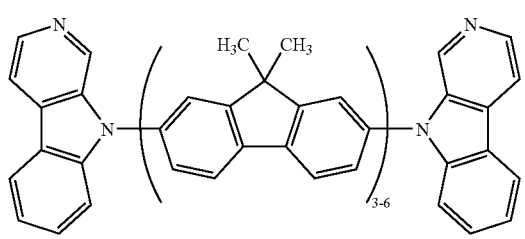
103a-d
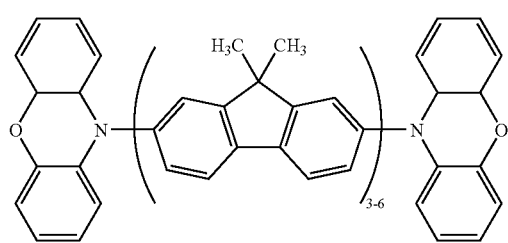
104a-d
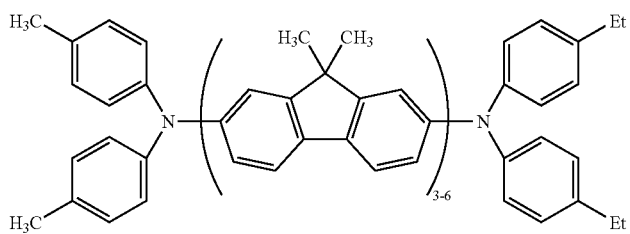
105a-d

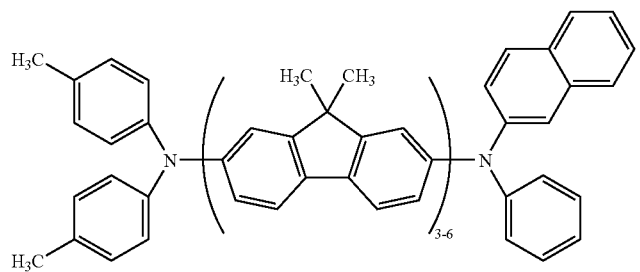
106a-d
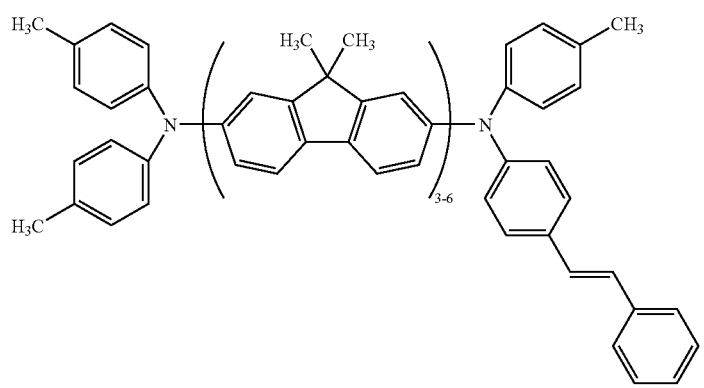
107a-d
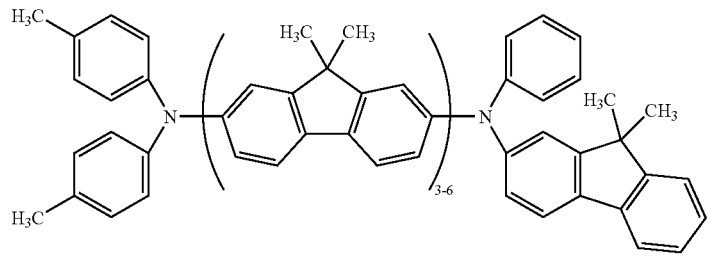
108a-d
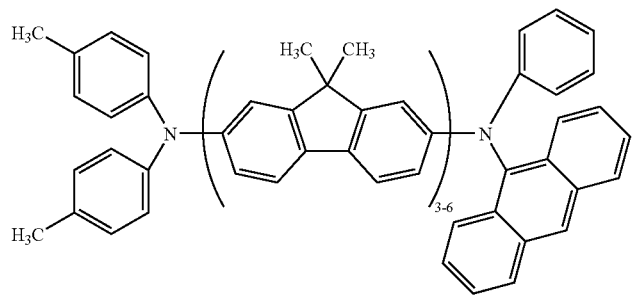
109a-d
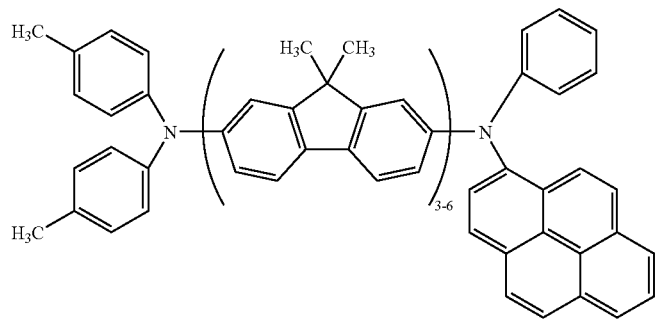
110a-d -continued

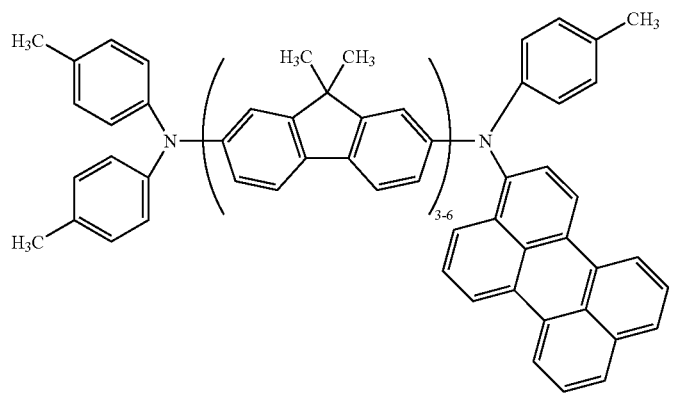

111a-d

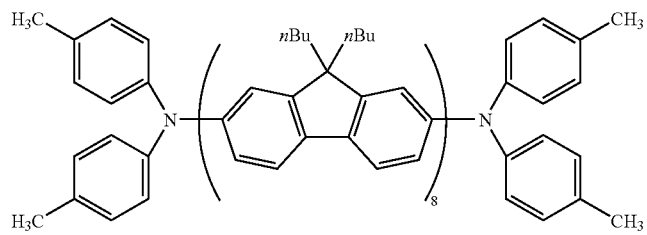

112

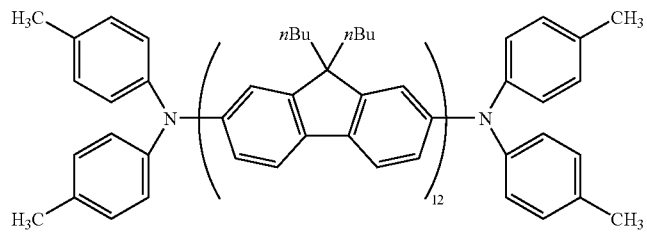

113

The compound of the present invention represented by the general formula (1) is suitable for use in a layer containing an organic compound in organic light-emitting devices, especially as a light-emitting layer, an electron-carrying layer, and a hole-carrying layer. Moreover, a layer that is formed by a vacuum vapor deposition method, solution coating method, etc., seldom suffers from crystallization and excels in stability with time.

The compound represented by the general formula (1) enables light emission that exhibits an emission spectrum with a narrower half peak width, that is, even further superior color purity, by introducing fluorenylene molecules that have rigid-rod structures to the main chain of the molecules. Moreover, the introduction of the structure suppresses Stokes shift, so that the absorption wavelength can be shifted to a longer wavelength while suppressing a shift of the emission wavelength, by adjusting the length of the fluorenylene chain. Thus, when the compound is used as a dopant material, this allows use of a host material that has a light emission spectrum on the relatively long wavelength side. Furthermore, emission colors can be adjusted by adjusting the substituents on nitrogen atoms, $X^1$ to $X^4$.

An estimation of oscillator strength by AM1/CNDOS calculations suggested that the oscillator strength could be increased by increasing the length of a fluorenylene chain from 2 to 3 or greater as in the present invention (calculations are performed on fluorenylene compounds composed of —N(Tol)$_2$ group and 9,9'-dimethylfluorenylene chain: oscillator strength 2.126527 for n=2; oscillator strength 2.974588 for n=3; oscillator strength 4.118244 for n=5). Calculations were carried out by means of Gaussian 98 software. The ground states of the molecules were determined by using semiempirical AM1 technique, and the energy level at the excited state was calculated while maintaining the molecular structure, by calculating configuration interactions using CNDOS method. Since an increase in oscillator strength leads to an increase in absorption intensity (Abs), energy transfer smoothly takes place between the compound and the host material that has an emission spectrum at a longer wavelength.

The compound represented by the general formula (1) can be used as both a dopant material and a host material in a light-emitting layer and therefore can provide a device that exhibits a high color purity, high emission efficiency, and long lifetime. In particular, when the compound is used as a dopant material and is combined with a suitable host material that easily causes energy transfer to take place between it and the dopant compound, a device that maintains a high color purity and has higher emission efficiency as well can be obtained.

When using the compound represented by the general formula (1) as a dopant material in a light-emitting layer, the concentration ratio of the dopant material to the host material is preferably 0.01% to 50%, more preferably 1% to 10%. Moreover, examples of preferred host materials include the following compounds, although of course they are not limited to these.

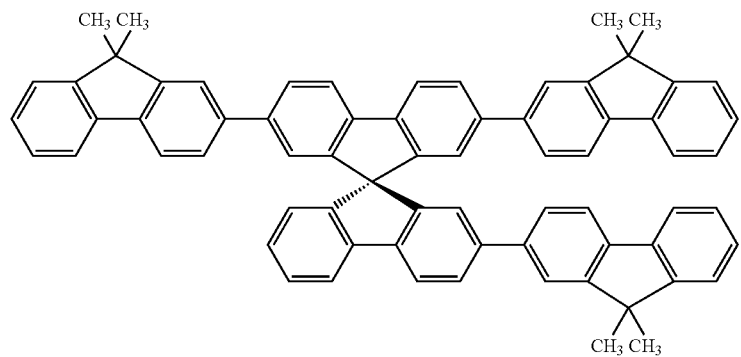
114
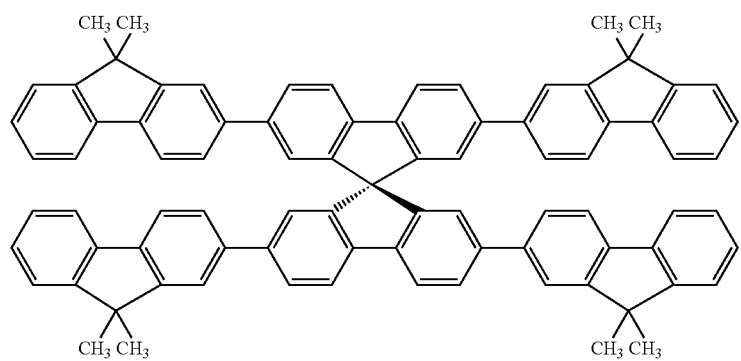
115
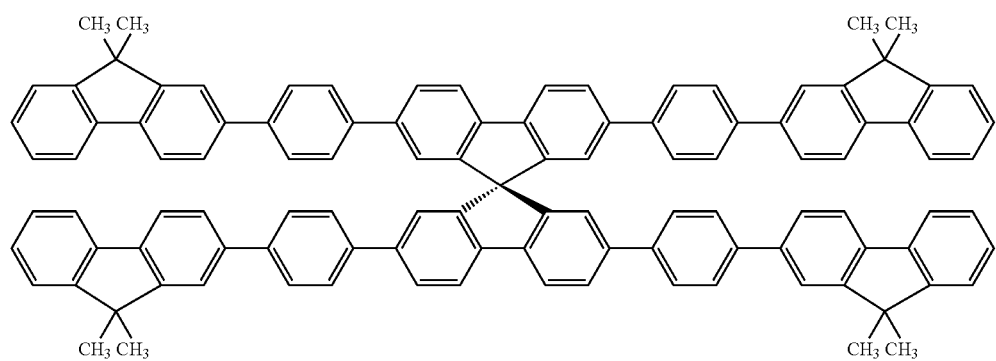
116
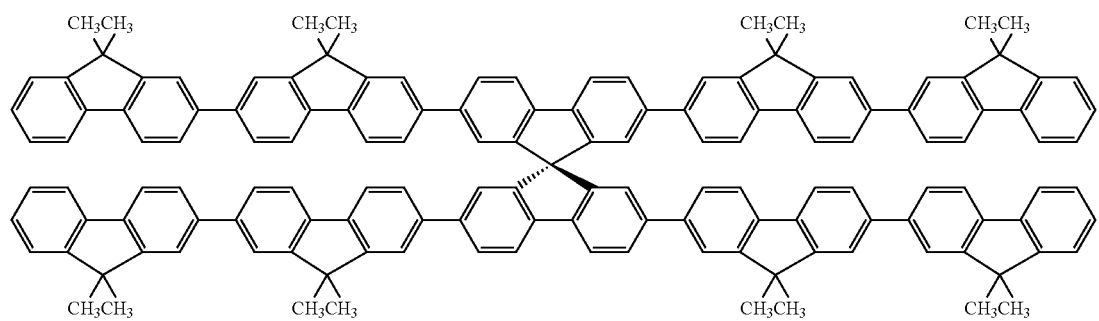
117

-continued
| | |
|---|---|
| 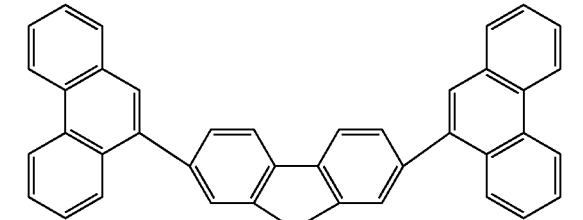 | 118 |
| | 119 |
| | 120 |
| | 121 |

-continued
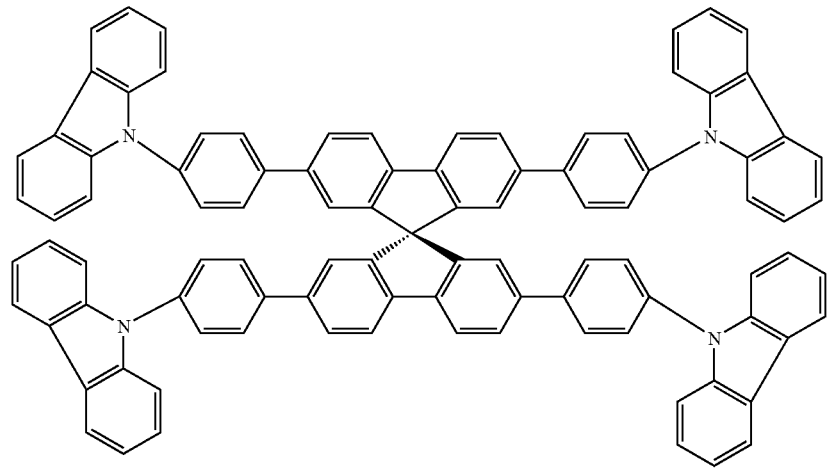
122
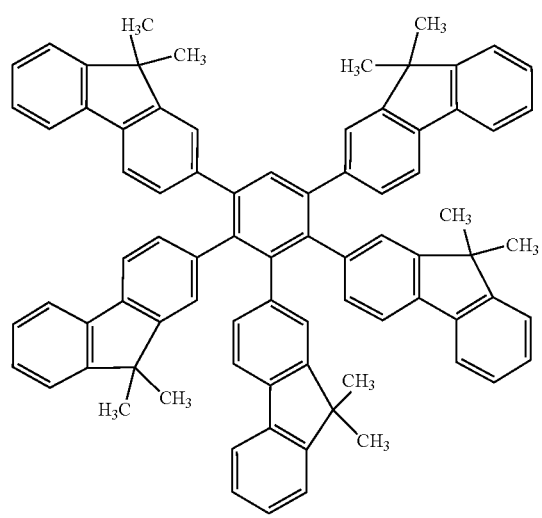
123

-continued
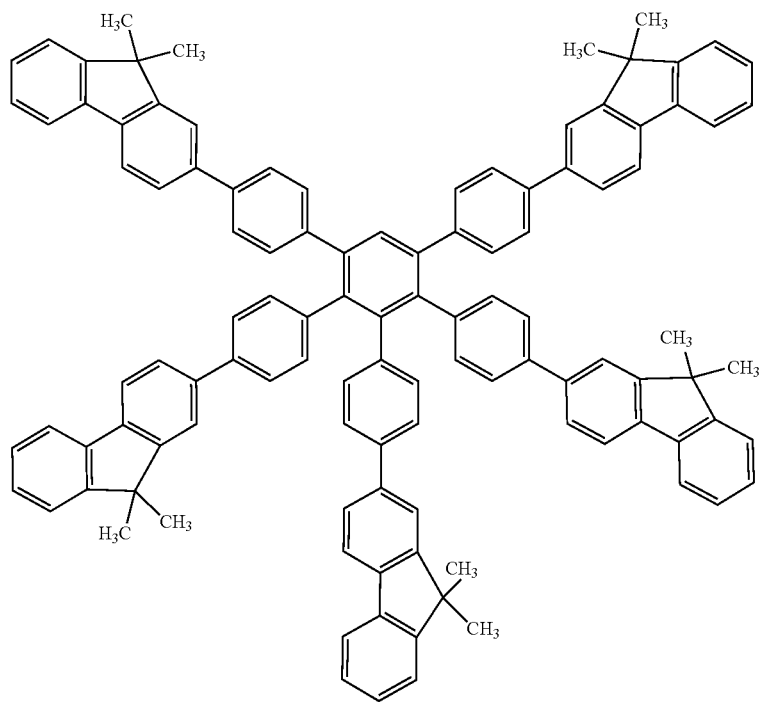
124
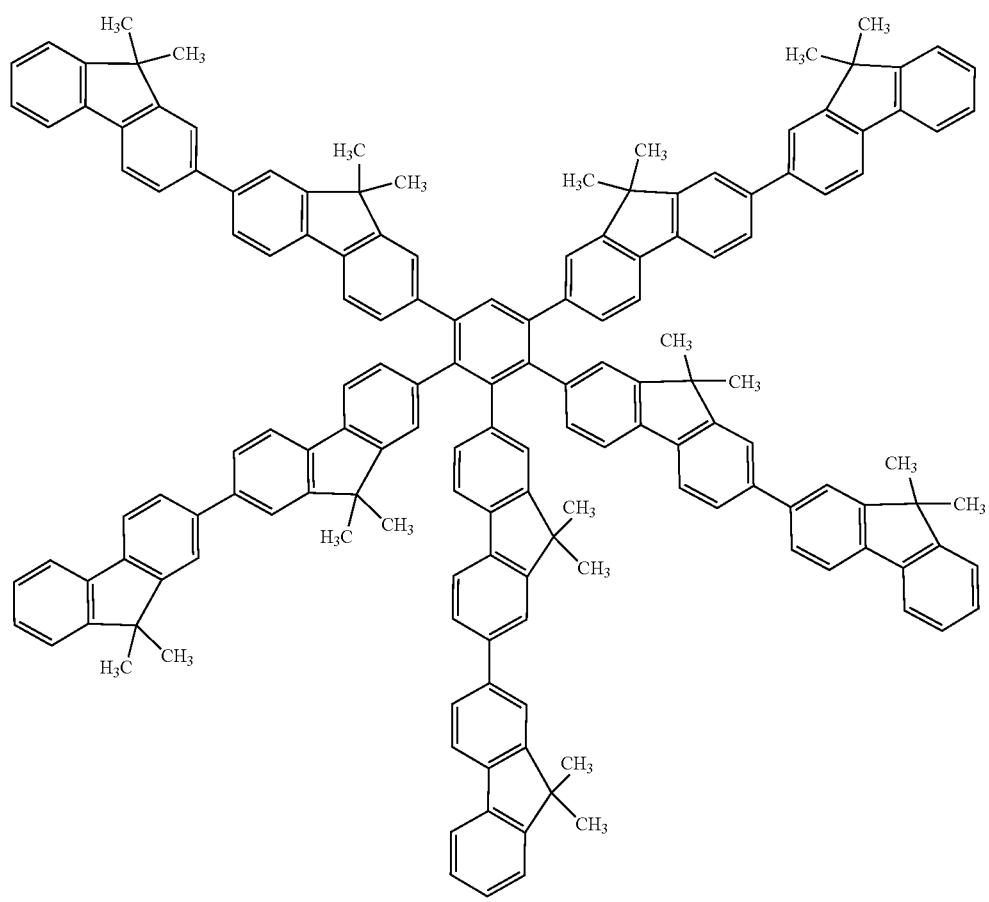
125

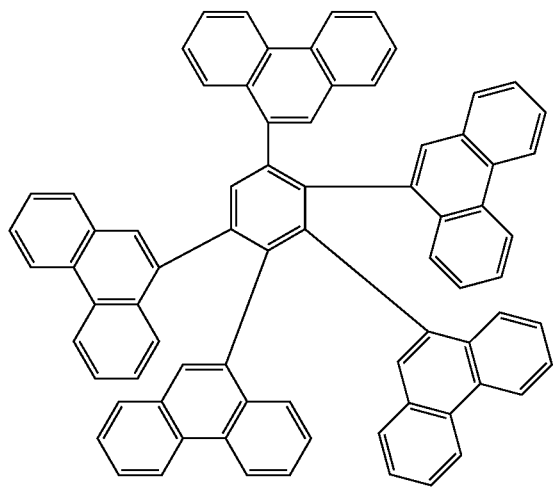
126
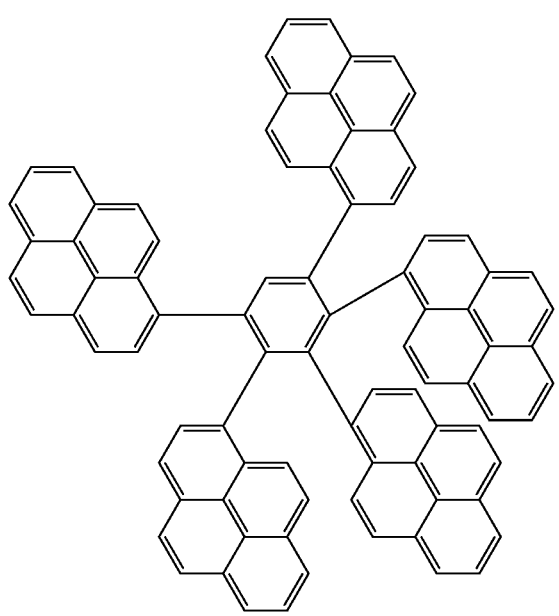
127

-continued
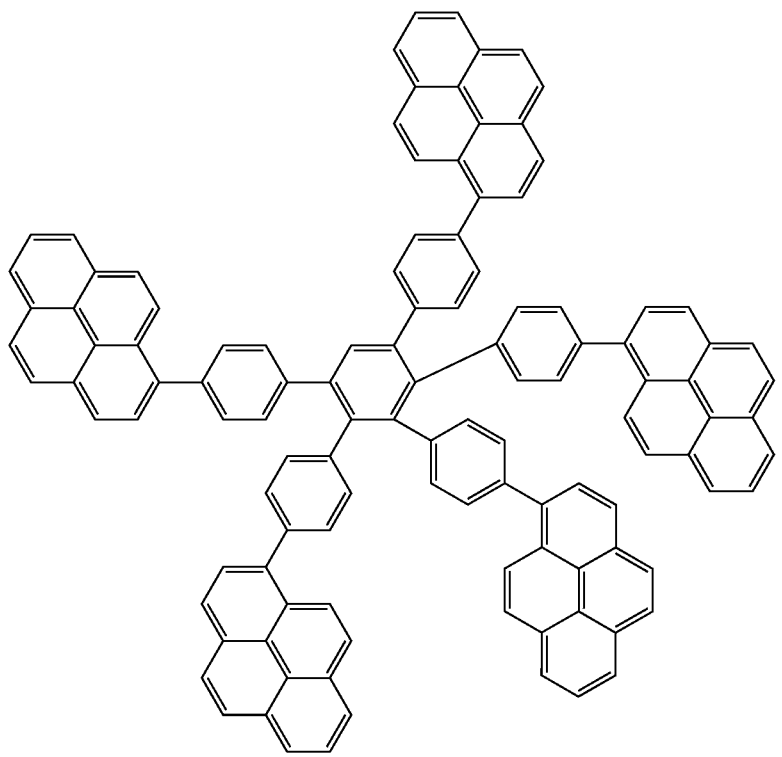
128
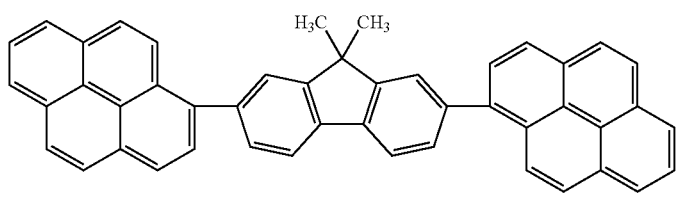
129
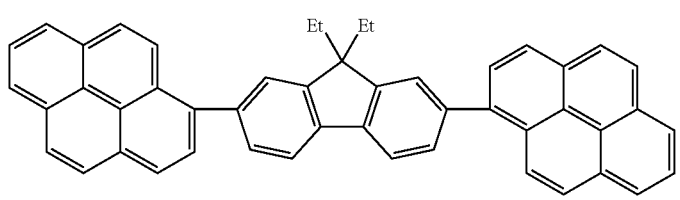
130
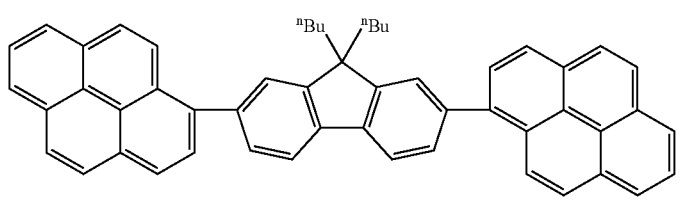
131
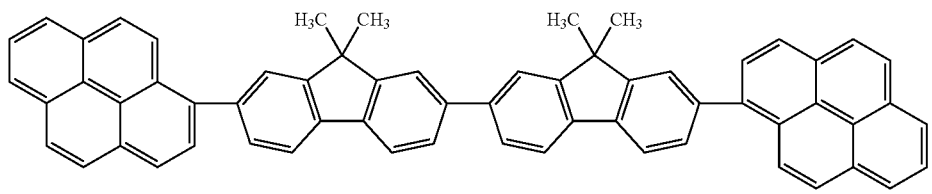
132

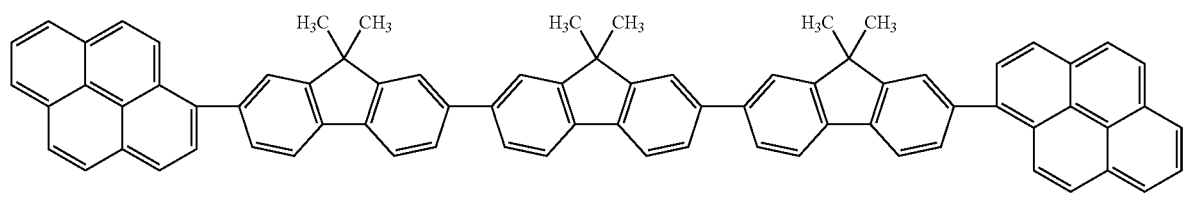
133
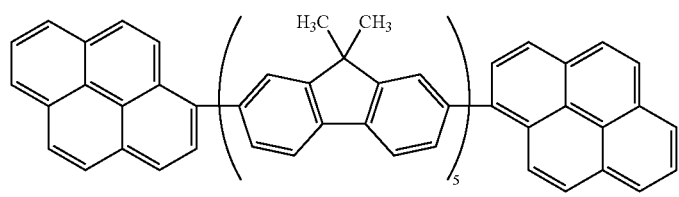
134
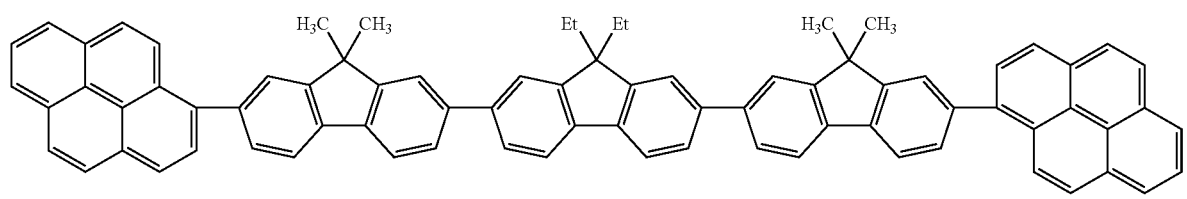
135
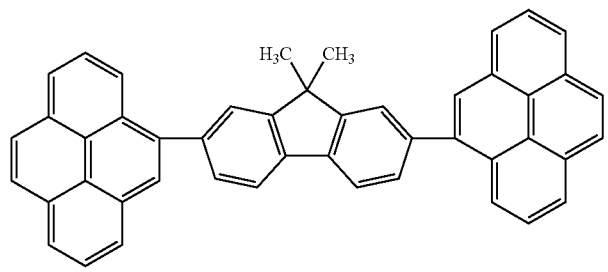
136
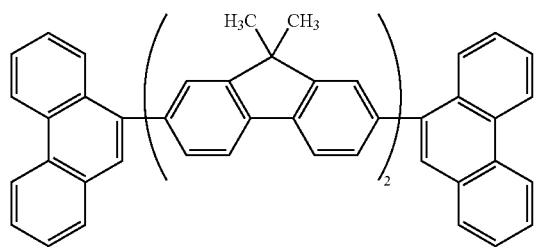
137
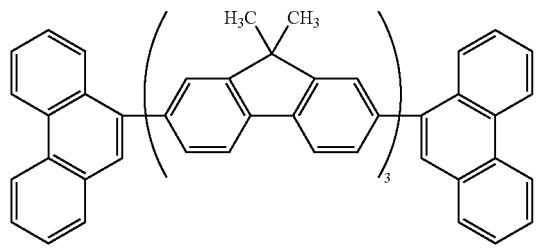
138

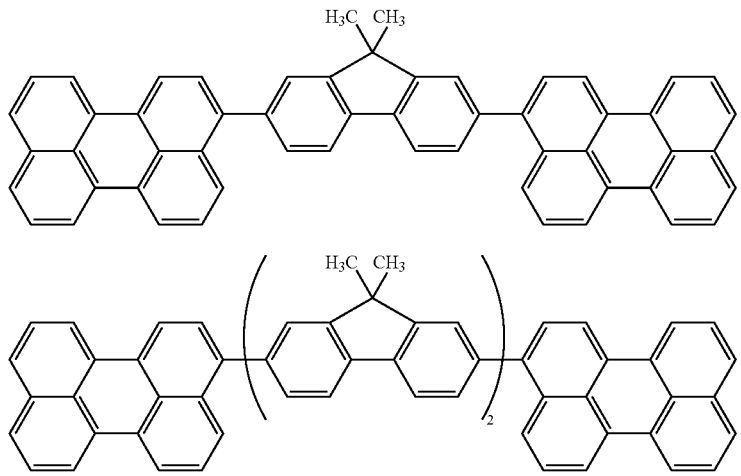

Next, the organic light-emitting device of the present invention will be explained in detail.

The organic light-emitting device of the present invention comprises a pair of electrodes comprising an anode and a cathode, and one or more layers that are sandwiched between the pair of electrodes and contain organic compounds, in which at least one of the layers containing the organic compounds, preferably a light-emitting layer, contains at least one of the fluorenylene compounds represented by the general formula (1).

Preferred examples of the organic light-emitting device of the present invention are shown in FIGS. 1 to 5.

FIG. 1 is a sectional view showing an example of the organic light-emitting device of the present invention. FIG. 1 shows a structure comprising a substrate 1 on which an anode 2, a light-emitting layer 3, and a cathode 4 are provided in this order. This type of light-emitting device is suitable for use in the case where the light-emitting device has that respectively have these characteristics are mixed for use in the device.

Figure 2:
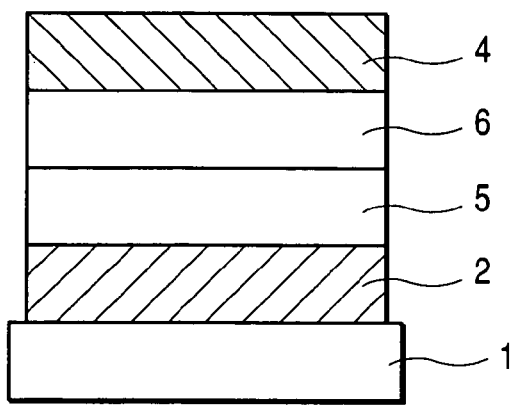
FIG. 2 is a sectional view showing another example of the organic light-emitting devices of the present invention.

FIG. 2 is a sectional view showing another example of the organic light-emitting device of the present invention. FIG. 2 shows a structure comprising a substrate 1 on which an anode 2, a hole-carrying layer 5, an electron-carrying layer 6, and a cathode 4 are provided in this order. This type of light-emitting device is useful when materials that have hole-carrying ability or electron-carrying ability, or both of these abilities are used in the respective layers and light-emitting materials are combined with hole-carrying materials or electron-carrying materials that have no light-emitting property. In this case, a light-emitting layer 3 is formed of either the hole-carrying layer 5 or the electron-carrying layer 6.

Figure 3:
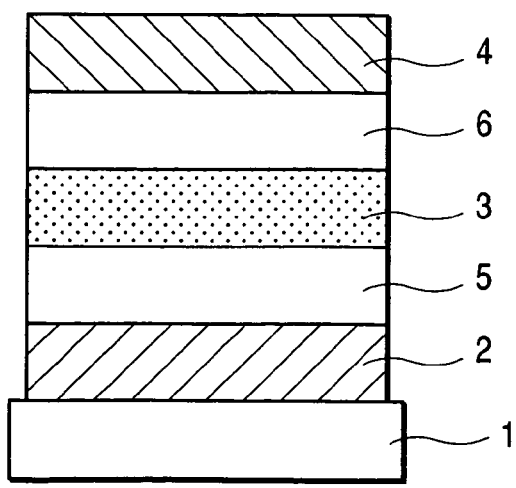
FIG. 3 is a sectional view showing still another example of the organic light-emitting devices of the present invention.

FIG. 3 is a sectional view showing another example of the organic light-emitting device of the present invention. FIG. 3 shows a structure comprising a substrate 1 on which an anode 2, a hole-carrying layer 5, a light-emitting layer 3, an electron-carrying layer 6, and a cathode 4 are provided in this order. In this case, carrier transfer function and light emission function are separated. This type of the light-emitting device is combined appropriately with compounds respectively having hole-carrying ability, electron-carrying ability, and light-emitting ability. Therefore, in addition to an extremely increased freedom in terms of selection of materials, the diversity of luminescent hues can be achieved because various compounds that have different emission wavelengths can be used. Moreover, it is possible to improve emission efficiency because the respective carriers or excitons are enclosed effectively in the light-emitting layer 3 provided in the center of the structure.

Figure 4:
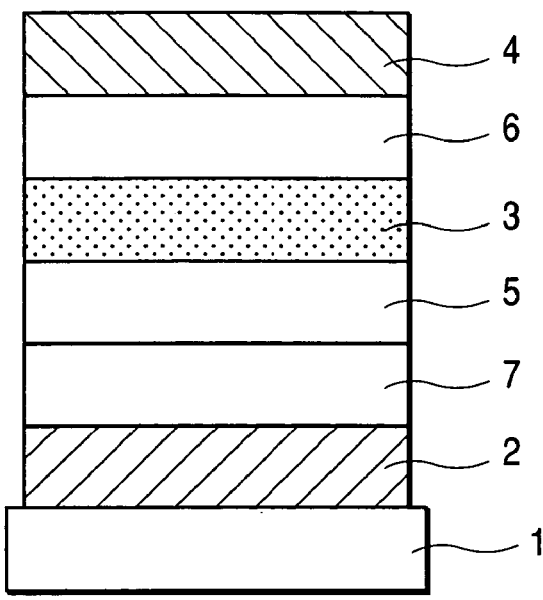
FIG. 4 is a sectional view showing yet another example of the organic light-emitting devices of the present invention.

FIG. 4 is a sectional view showing another example of the organic light-emitting device of the present invention. In contrast with FIG. 3, FIG. 4 shows a structure in which a hole-injecting layer 7 is inserted between an anode 2 and a hole-carrying layer 5. This structure is effective for improving the adhesion between the anode 2 and the hole-carrying layer 5 or the hole injecting property, thus effectively achieving a reduction in required voltage.

Figure 5:
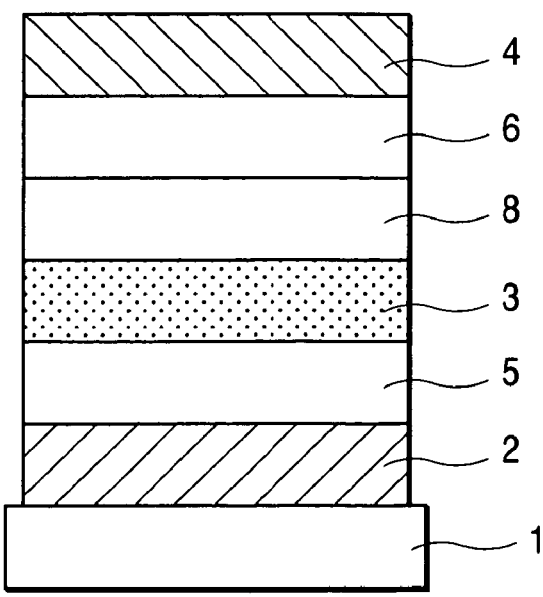
FIG. 5 is a sectional view showing yet still another example of the organic light-emitting devices of the present invention.

FIG. 5 is a sectional view showing another example of the organic light-emitting device of the present invention. In contrast with FIG. 3, FIG. 5 shows a structure comprising a layer (hole-blocking layer 8) that prevents holes or excitons from passing toward a cathode 4 is inserted between a light-emitting layer 3 and an electron-carrying layer 6. This structure effectively enables an improvement in emission efficiency by the use of a compound having a very high ionization potential as the hole-blocking layer 8.

However, FIGS. 1 to 5 merely show very basic device structures, to which structures of the organic light-emitting device using the compound of the present invention are not limited. For example, various layer structures can be prepared, such as providing an insulating layer in the interface between an electrode and an organic layer, providing a adhesion layer or an interfering layer, preparing a hole-carrying layer composed of two layers having different ionization potentials, etc.

The compound represented by the general formula (1) can be used in any of the forms depicted in FIGS. 1 to 5.

The present invention is particularly directed to a case where the compound represented by the general formula (1) is used as a constituent of a light-emitting layer and further, if needed, host materials such as the above exemplified compounds 114 to 140 are used. However, hole-carrying compounds, light-emitting compounds, or electron-carrying compounds that have already been known can be used together therewith if needed.

Examples of these compounds are cited below.
Hole-Carrying Compounds
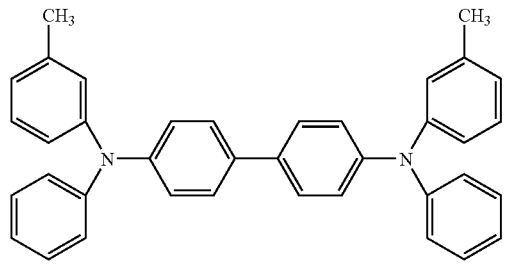
TPD
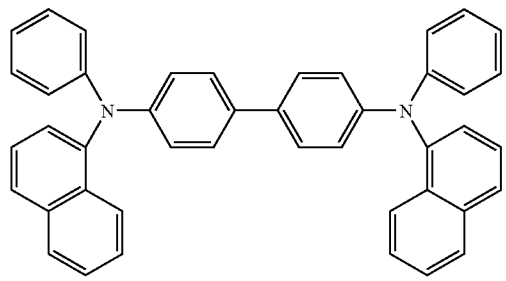
α-NPD
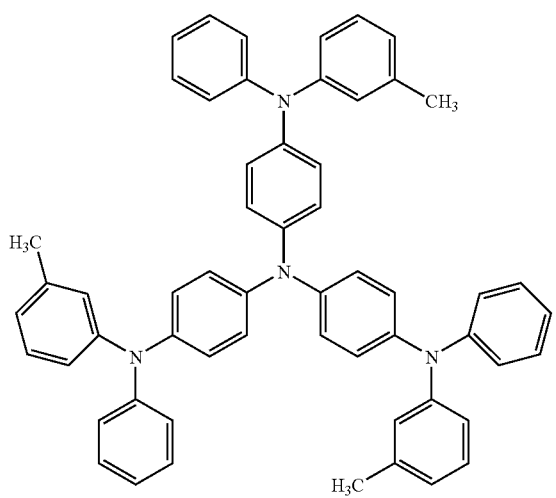
m-MTDATA
-continued
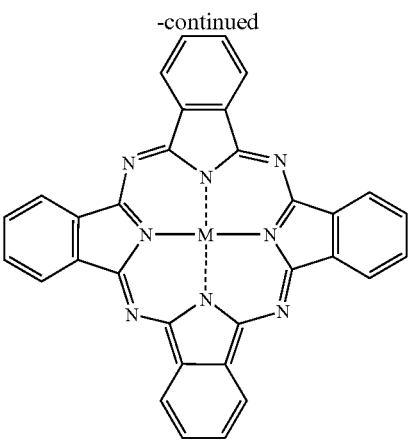
Pc-M
M: Cu, Mg, AlCl, TiO, SiCl$_2$, Zn, Sn, MnCl, GaCl, etc
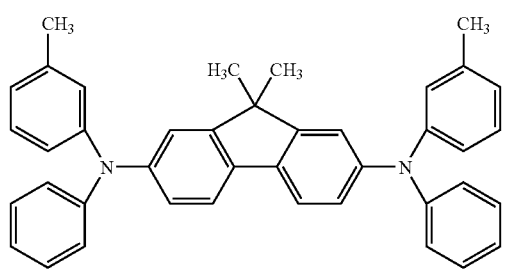
DTDPFL
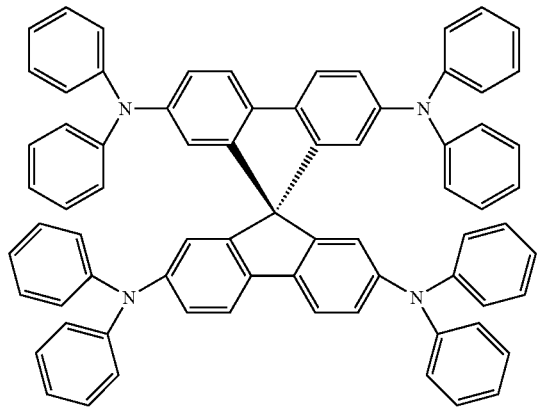
spiro-TPD
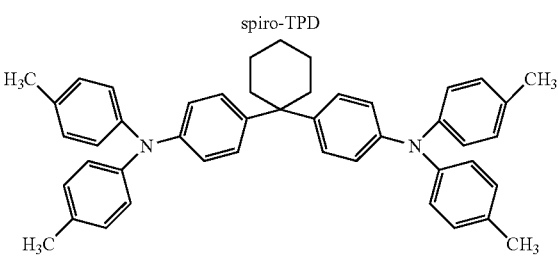
TPAC -continued
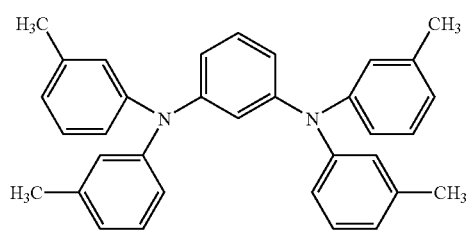
PDA
Electron-Carrying Compounds
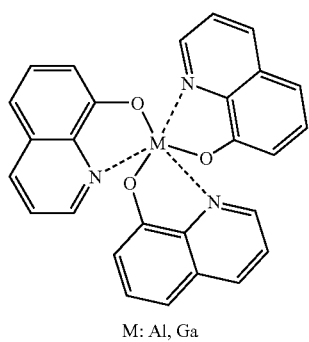
M: Al, Ga
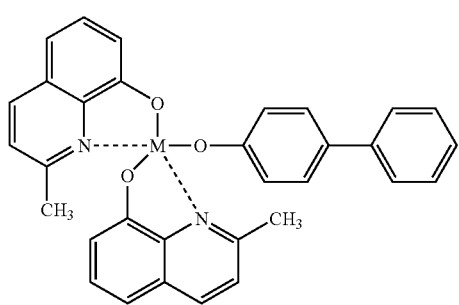
M: Al, Ga
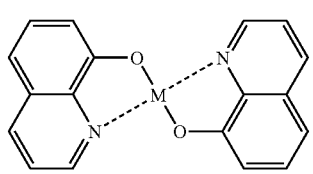
M: Zn, Mg, Be
-continued
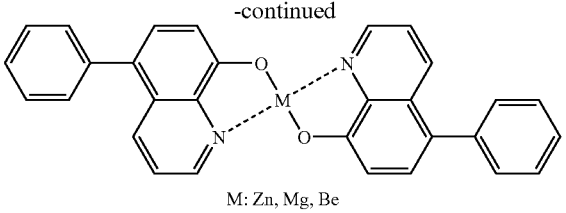
M: Zn, Mg, Be
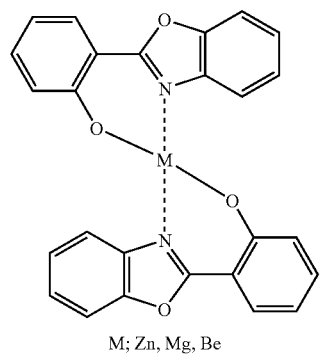
M; Zn, Mg, Be
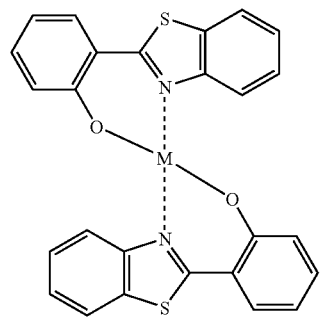
M; Zn, Mg, Be
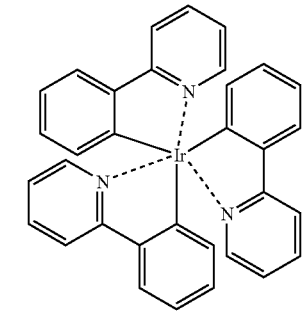
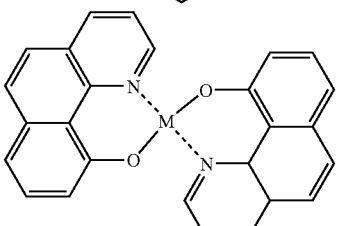
M: Zn, Mg, Be -continued
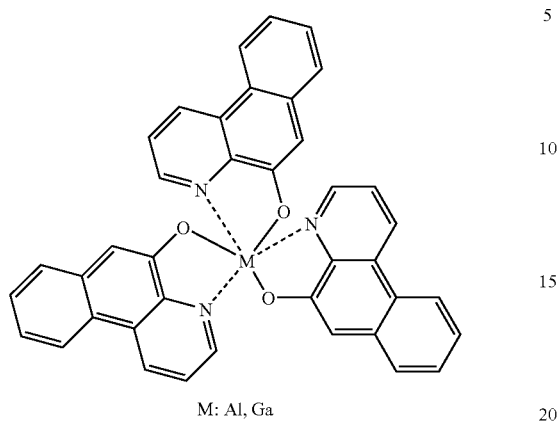
M: Al, Ga
Light-Emitting Materials
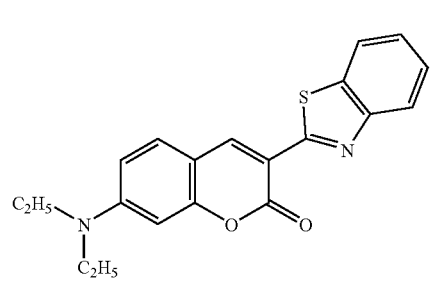
Coumarin6
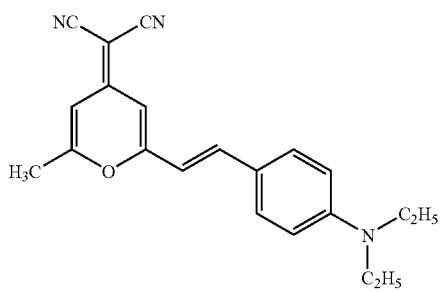
DCM-1
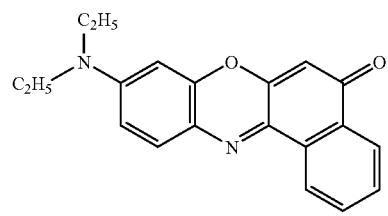
Nile red
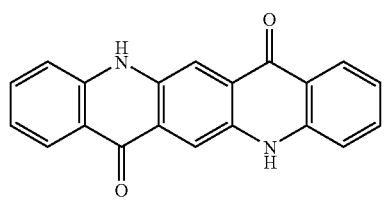
Quinacridone
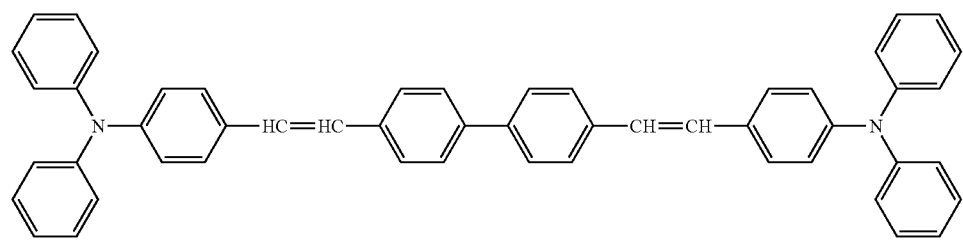
DTPABVi

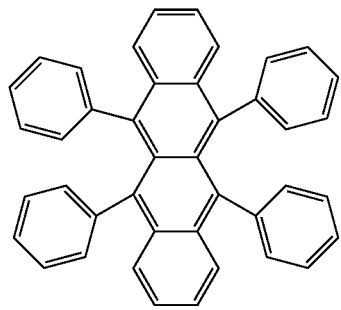
Rubrene
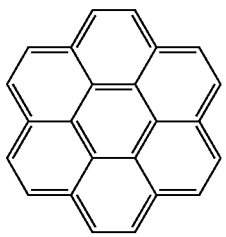
Coronene
Light-Emitting Layer Matrix Materials and Electron-Carrying Materials
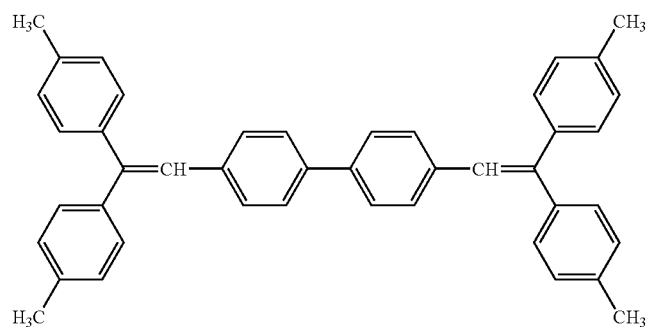
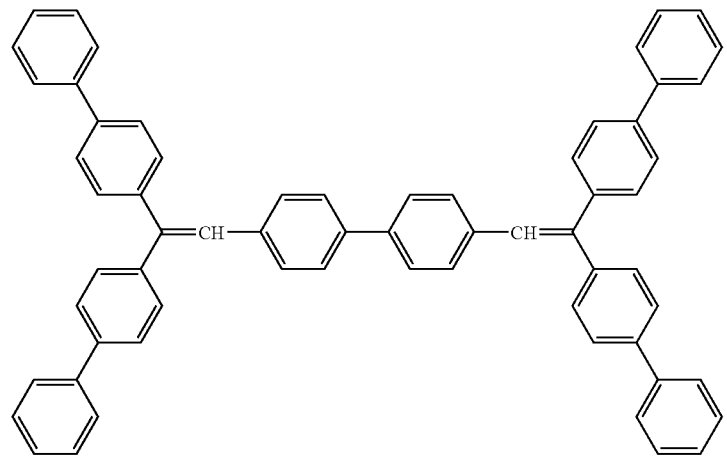
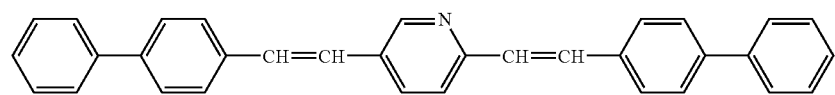

-continued
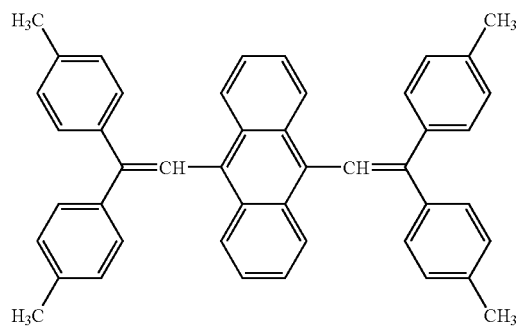
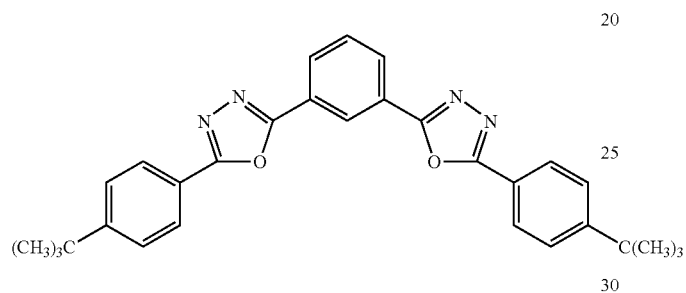
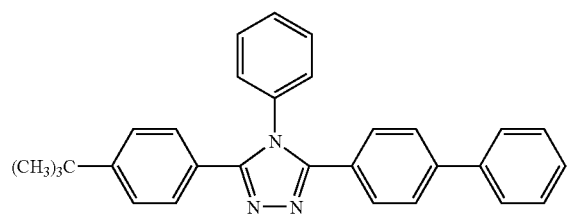
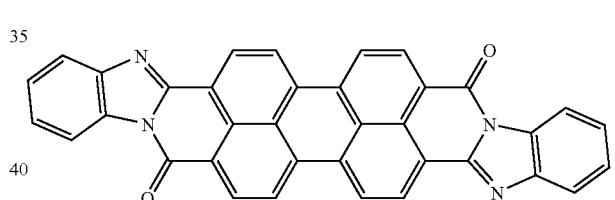
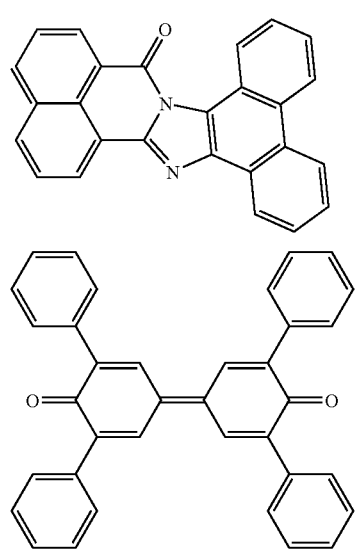
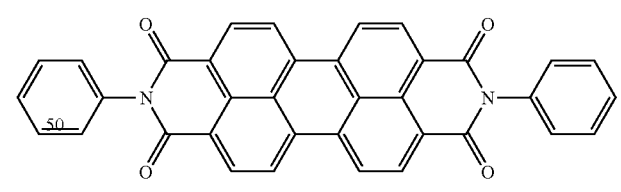

Polymeric Hole-Carrying Materials
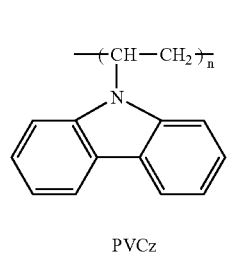
PVCz
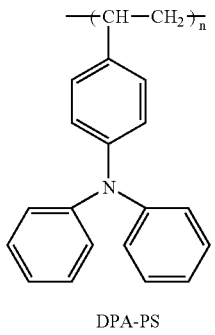
DPA-PS
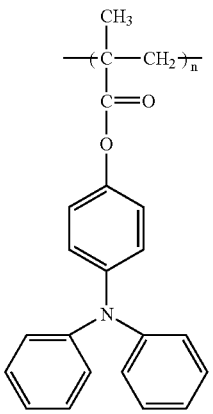
TPA-PMMA
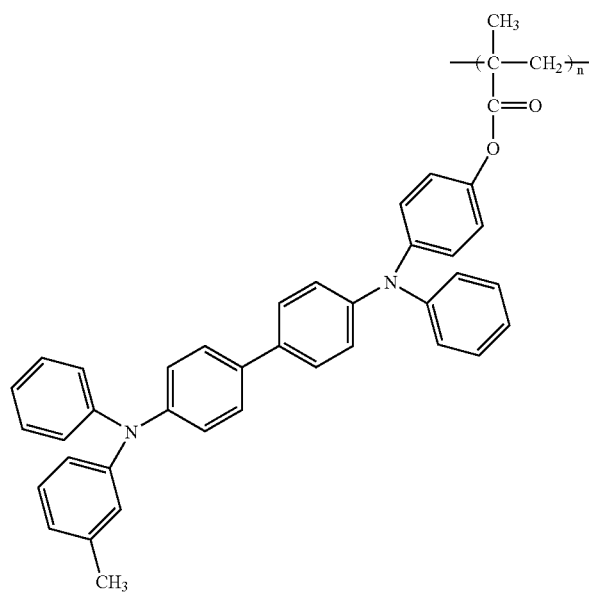
TPD-PMMA -continued
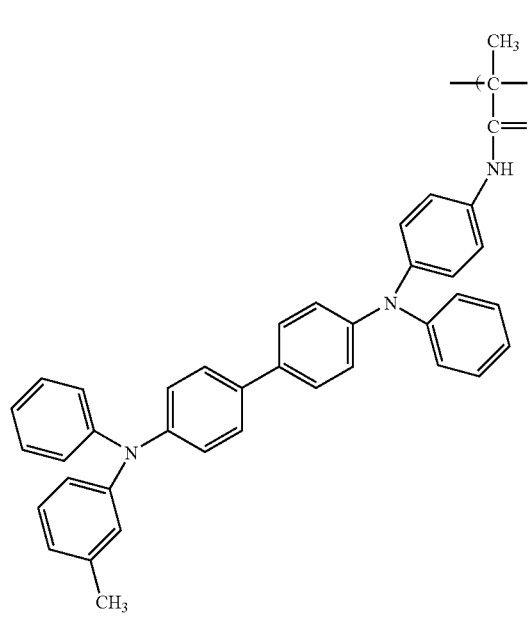
TPD-PMAA
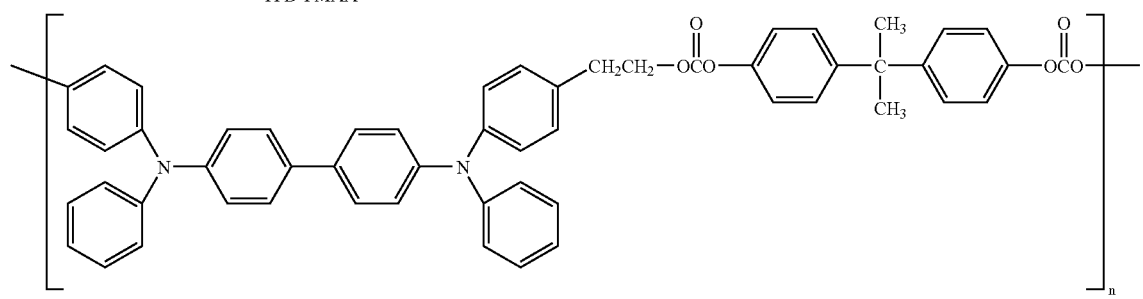
TPD-PCA
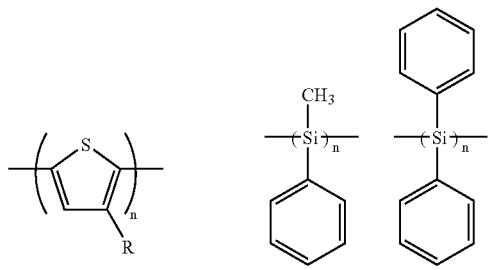
R: $C_6H_{13}$, $C_8H_{17}$, $C_{12}H_{25}$
Poly thiophene
Polysilane
Polymeric Light-Emitting Materials and Charge-Carrying Materials
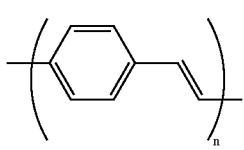
-continued
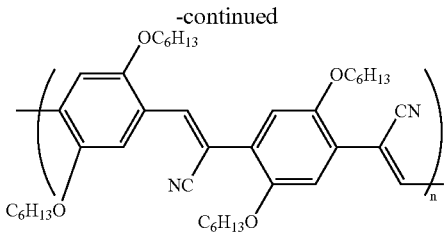

-continued

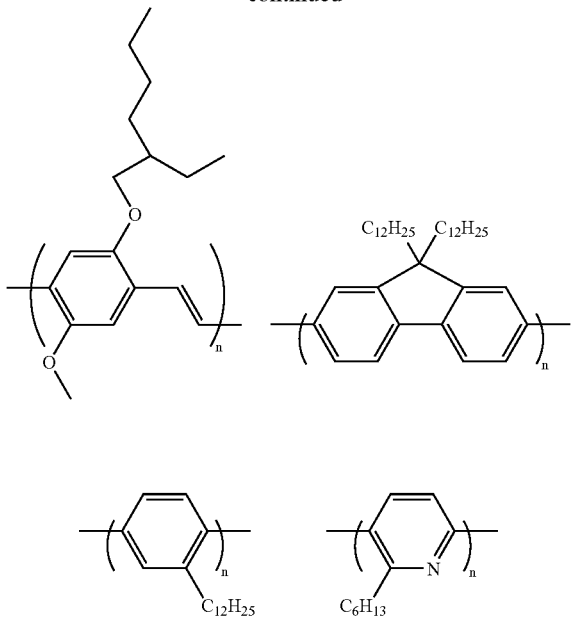

In the organic light-emitting device of the present invention, a layer containing the compound represented by the general formula (1) and a layer containing another organic compound can be formed into a thin film generally by a vacuum vapor deposition method or by a coating method after dissolving the compound in a suitable solvent. In particular, when film formation is performed by a coating method, the compounds can be combined with a suitable binding resin to form a film.

The above binding resin can be selected from various binding resins, such as polyvinylcarbazole resin, polycarbonate resin, polyester resin, polyarylate resin, polystyrene resin, acrylic resin, methacrylic resin, butyral resin, poly(vinyl acetal) resin, diallyl phthalate resin, phenol resin, epoxy resin, silicone resin, polysulfone resin, urea resin, etc., although they are not limited to the above. Moreover, those resins may be used singly, or one or more resins may be mixed with each another as a copolymer.

The anode material is preferably selected from materials having the greatest work function possible. For example, metal simple substances such as gold, platinum, nickel, palladium, cobalt, selenium, and vanadium, or alloys of these, metal oxides such as tin oxide, zinc oxide, indium-tin oxide (ITO), and indium-zinc oxide can be used. Furthermore, conductive polymers such as polyaniline, polypyrrole, polythiophene, and polyphenylene sulfide can also be used. These electrode materials may be used singly or in combination with each another.

On the other hand, the cathode materials are preferably selected from materials having a small work function. For example, metal simple substances such as lithium, sodium, potassium, cesium, calcium, magnesium, aluminum, indium, silver, lead, tin, and chromium, or alloys of these can be used. Metal oxides such as indium-tin oxide (ITO) can also be used. Additionally, the cathode may be structured as a single layer or multiple layers.

The substrates for use in the present invention are not particularly limited. For example, opaque substrates such as metal substrates and ceramic substrates, or transparent substrates such as a glass, quartz, and plastic sheet are used. Moreover, emitted light can be controlled by applying a color filter film, a fluorescent color conversion filter film, a dielectric reflection film, etc. to the substrate.

Besides, a protection layer or a seal layer may be provided in a prepared device for the purpose of preventing the device from coming into contact with oxygen or moisture. Examples of the materials for use in the protection layer include: inorganic material films such as a diamond thin film, metal oxides, and metal nitrides; polymer films such as a fluororesin, poly(p-xylene), polyethylene, silicone resin, and polystyrene resin; and further light-setting resins, etc. Furthermore, the prepared device can be packaged with a suitable seal resin by covering the device with a glass, a gas-impermeable film, metal, etc.

EXAMPLES

The present invention will be specifically explained with reference to the following examples, but the present invention is not limited to these examples.

Example 1

(Method for Producing the Exemplified Compound No. 40a)

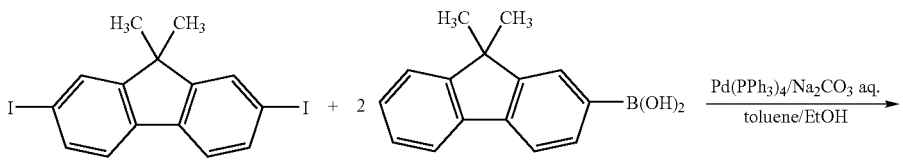

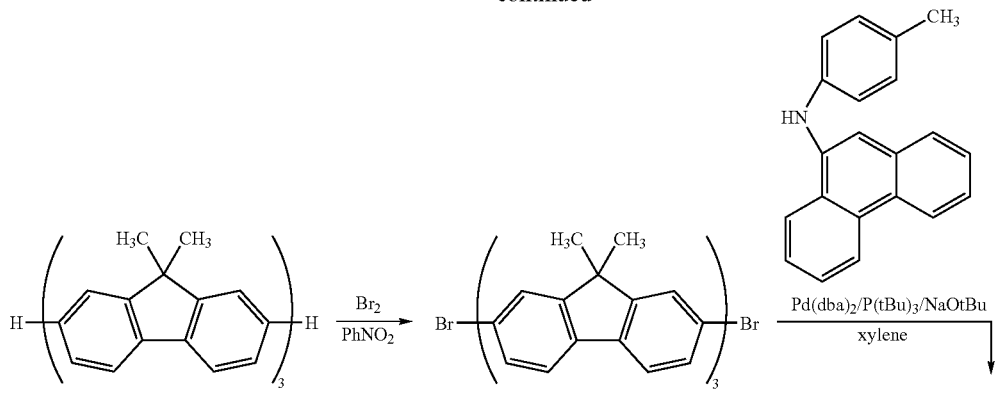

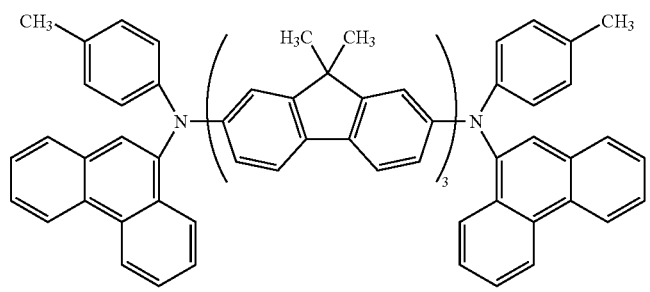

40a

Under nitrogen flow, 5 g (11.2 mmol) of 2,7-diiodo-9,9-dimethylfluorene, 9 g (24.7 mmol) of 9,9-dimethylfluorene-2-boronic acid were dissolved in a mixed solvent of 200 ml of degassed toluene and 100 ml of ethanol and were stirred. To this solution, 245 ml of an aqueous sodium carbonate solution prepared by dissolving 51 g of sodium carbonate anhydride in 250 ml of water was added dropwise. After stirring for 30 minutes, 1.42 g (1.23 mmol) of tetrakis(triphenylphosphine) palladium was added. The mixture was then heated and stirred for about 3 hours on an oil bath heated to 80° C. After cooling the reaction solution down to room temperature, 100 ml of water and 100 ml of ethyl acetate were added thereto, and then the water phase and the organic phase were separated. The water phase was then extracted with toluene and ethyl acetate. The extract was added to the organic phase obtained previously and was dried with sodium sulfate. After distilling away the solvents, the residue was purified by column chromatography on silica gel (toluene:hexane=1:2) and thus 4.9 g of tris(9,9-dimethylfluorenylene) was obtained.

Under nitrogen atmosphere, 4.5 g (7.79 mmol) of tris(9,9-dimethylfluorenylene) was heated and dissolved in 150 ml of nitrobenzene. Then, 2.5 g (15.6 mmol) of bromine was added dropwise thereto slowly on an oil bath heated to 60° C. and were further stirred for about 2 hours. After cooling the reaction solution with an ice bath and then stirring for a while, to room temperature, precipitates were filtrated. The precipitates were recrystallized from toluene, and after filtration and drying thereof, 3.4 g of dibromide of tris(9,9-dimethylfluorenylene) was obtained.

Under nitrogen atmosphere, 156 mg (0.272 mmol) of palladium bis(benzylidene acetone) and 330 mg (1.63 mmol) of tri-tert-butylphosphine were dissolved in 20 ml of xylene and were stirred for 15 minutes at room temperature. To this solution, 1 g (1.36 mmol) of dibromide of tris(9,9-dimethylfluorenylene) dissolved in 50 ml of xylene was added dropwise and stirred for 30 minutes on an oil bath heated to 50° C. Then, 1.15 g (4.08 mmol) of N-(4-methylphenyl)-N-(9-phenanthryl)amine was dissolved in 20 ml of xylene and added dropwise to the solution. Subsequently, 588 mg (6.12 mmol) of sodium tert-butoxide was added thereto. The mixture was then heated and stirred for about 5 hours on an oil bath heated to 130° C. After cooling the reaction solution down to room temperature, 50 ml of water was added and then the water phase and the organic phase were separated. The water phase was then extracted with toluene and ethyl acetate. The extract was added to the organic phase obtained previously and was dried with magnesium sulfate. After distilling away the solvents, the residue was purified by column chromatography on silica gel (toluene:hexane=1:2) and thus 1.2 g of the exemplified compound No. 40a was obtained.

Example 2

(Method for Producing the Exemplified Compound No. 71b)

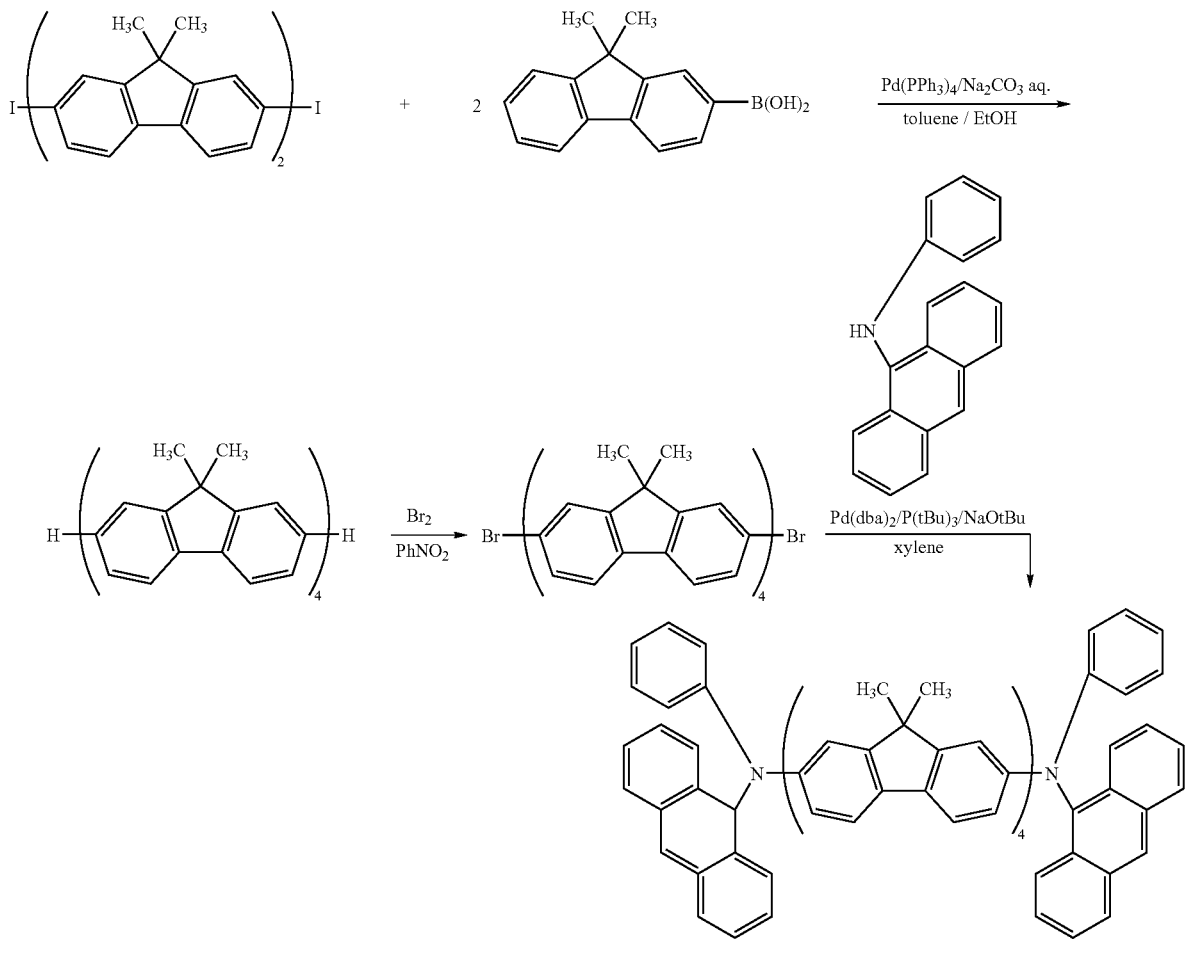

Under nitrogen flow, 5 g (7.84 mmol) of bis(2-iodo-9,9-dimethylfluorene), 6.26 g (17.2 mmol) of 9,9-dimethylfluorene-2-boronic acid were dissolved in a mixed solvent of 200 ml of degassed toluene and 100 ml of ethanol, and were stirred. To this solution, 170 ml of an aqueous sodium carbonate solution prepared by dissolving 36 g of sodium carbonate anhydride in 180 ml of water was added dropwise. After stirring this for 30 minutes, 994 mg (0.86 mmol) of tetrakis(triphenylphosphine) palladium was added. The mixture was then heated and stirred for about 3 hours on an oil bath heated to 80° C. After cooling the reaction solution down to room temperature, 100 ml of water and 100 ml of ethyl acetate were added, and then the water phase and the organic phase were separated. The water phase was then extracted with toluene and ethyl acetate. The extract was added to the organic phase obtained previously and was dried with sodium sulfate., After distilling away the solvents, the residue was purified by column chromatography on silica gel (toluene:hexane=1:2) and thus 3.92 g of tetrakis (9,9-dimethylfluorenylene) was obtained.

Under nitrogen atmosphere, 3 g (3.90 mmol) of tetrakis (9,9-dimethylfluorenylene) was heated and dissolved in 150 ml of nitrobenzene. Then, 1.4 g (7.80 mmol) of bromine was added dropwise thereto slowly on an oil bath heated to 60° C. and were further stirred for about 2 hours. After cooling the reaction solution with an ice bath and then stirring for a while, precipitates were filtrated. The precipitates were recrystallized from xylene, and after filtration and drying thereof, 2 g of dibromide of tetrakis(9,9-dimethylfluorenylene) was obtained.

Under nitrogen atmosphere, 124 mg (0.216 mmol) of palladium bis(benzylidene acetone) and 130 mg (0.648 mmol) of tri-tert-butylphosphine were dissolved in 20 ml of xylene and were stirred for 15 minutes at room temperature. To this solution, 1 g (1.08 mmol) of dibromide of tetrakis (9,9-dimethylfluorenylene) dissolved in 50 ml of xylene was added dropwise and stirred for 30 minutes on an oil bath heated to 50° C. Then, 694 mg (2.59 mmol) of N-(1-anthracenyl)-N-(phenyl)amine was dissolved in 20 ml of xylene and added dropwise to the solution. Subsequently, 374 mg (3.89 mmol) of sodium tert-butoxide was added. The mixture was then heated and stirred for about 7 hours on an oil bath heated to 130° C. After cooling the reaction solution down to room temperature, 50 ml of water was added and then the water phase and the organic phase were separated. The water phase was then extracted with toluene and ethyl acetate. The extract was added to the organic phase obtained previously and was dried with magnesium sulfate. After distilling away the solvents, the residue was purified by column chromatography on silica gel (toluene:hexane=1:2) and thus 900 mg of the exemplified compound No. 71b was obtained.

Example 3

An organic light-emitting device having a structure shown in FIG. 3 was produced by the following method.

A transparent and conductive supporting substrate was used which was produced by forming a film of indium-tin oxide (ITO) as an anode 2 on a glass substrate as a substrate 1, the film having a film thickness of 120 nm by means of sputtering method. This substrate was cleaned ultrasonically with acetone and isopropyl alcohol (IPA) in this order. After a boiling cleaning with IPA, the substrate was then dried. The substrate was further cleaned with UV/ozone and then was used as a transparent and conductive supporting substrate.

Using the compound represented by the following structural formula as a hole-carrying material, a chloroform solution was prepared so that the concentration thereof was 0.5% by weight.

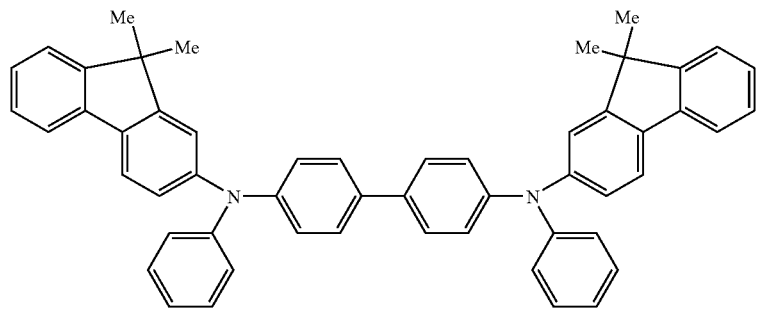

This solution was added dropwise onto the above-mentioned anode 2, so that spin coating was carried out to form a film, firstly with the revolutions kept at 500 rpm for 10 seconds, secondly with the revolutions kept at 1000 rpm for 1 minute. After forming the film, the film was dried for 10 minutes in a vacuum oven at 80° C., so that the solvents in the thin film were fully removed. The thickness of the hole-carrying layer thus formed was 50 nm.

Then, the above exemplified compound No. 2a was deposited as a light-emitting layer 3 on a hole-carrying layer 5, so that a light-emitting layer 3 having a thickness of 20 nm was provided. The degree of vacuum at the vapor deposition was $1.0\times10^{-4}$ Pa, and the film forming rate was 0.2 to 0.3 nm per second.

Furthermore, a film of aluminum quinolinol (Alq3) as an electron-carrying layer 6 was formed by vacuum vapor deposition method so as to have a thickness of 40 nm. The degree of vacuum at the vapor deposition was $1.0\times10^{-4}$ Pa, and the film forming rate was 0.2 to 0.3 nm per second.

Next, using a deposition material comprising an aluminum-lithium alloy (having a lithium concentration of 1 atom %), a metal film layer having a thickness of 10 nm was formed on the above organic layer by means of vacuum vapor deposition method. Subsequently, an aluminum film was further provided so as to have a thickness of 150 nm by vacuum vapor deposition method. Thus, an organic light-emitting device having an aluminum-lithium alloy film as an electron-injecting electrode (cathode 4) was prepared. The degree of vacuum at the vapor deposition was $1.0\times10^{-4}$ Pa, and the film forming rate was 1.0 to 1.2 nm per second.

The organic electroluminescent device thus obtained was covered with a protection glass in a dry air atmosphere and sealed with an acrylic resin adhesive, so that it is not deteriorated due to moisture adsorption.

Using an ITO electrode (anode 2) as a positive electrode and an Al—Li electrode (cathode 4) as a negative electrode, a voltage of 6 V was applied to the device thus obtained, so that a light emission having an emission brightness of 1600 cd/m$^2$, a maximum brightness of 9100 cd/m$^2$, and an emission efficiency of 1.25 lm/W was observed.

Examples 4 to 9

Devices were prepared and examined in a similar manner as in Example 3 except for using the compounds shown in Table 1 instead of the exemplified compound No. 2a. The results are shown in Table 1.

TABLE 1

| Example | Exemplified Compound No. | Applied Voltage (V) | Brightness (cd/m$^2$) | Maximum brightness (cd/m$^2$) | Efficiency (lm/w) |
|---|---|---|---|---|---|
| 4 | 13c | 6 | 1830 | 10500 | 1.35 |
| 5 | 40a | 6 | 1640 | 9870 | 1.28 |
| 6 | 50a | 6 | 1960 | 11200 | 1.40 |
| 7 | 71b | 5 | 1260 | 13150 | 1.46 |
| 8 | 80a | 5 | 1430 | 14250 | 1.49 |
| 9 | 108a | 6 | 2090 | 11310 | 1.41 |

Example 10

The organic light-emitting device that has a structure shown in FIG. 3 was prepared by the following method.

A hole-carrying layer 5 was formed on a transparent and conductive supporting substrate in a similar manner as in Example 3.

Subsequently, the above exemplified compound No. 6b was deposited as a light-emitting layer on the hole-carrying layer 5, so that a light-emitting layer 3 having a thickness of 20 nm was provided. The degree of vacuum at the vapor deposition was 1.0×10⁻⁴ Pa, and the film forming rate was 0.2 to 0.3 nm per second.

Furthermore, an electron-carrying layer 6 was formed by forming a film of bathophenanthroline (Bphen) having a thickness of 40 nm by vacuum vapor deposition method. The degree of vacuum at the vapor deposition was $1.0 \times 10^{-4}$ Pa, and the film forming rate was 0.2 to 0.3 nm per second.

Next, after forming a cathode 4 in a similar manner as in Example 1, the device was sealed.

Using an ITO electrode (anode 2) as a positive electrode and an Al—Li electrode (cathode 4) as a negative electrode, a voltage of 6 V was applied to the device thus obtained, so that a light emission having an emission brightness of 2250 cd/m², a maximum brightness of 11750 cd/m², and an emission efficiency of 1.39 lm/W was observed.

Examples 11 to 14

Devices were prepared and examined in a similar manner as in Example 10 except for using the compounds shown in Table 2 instead of the exemplified compound No. 6b. The results are shown in Table 2.

TABLE 2

| Example | Exemplified Compound No. | Applied Voltage (V) | Brightness (cd/m²) | Maximum brightness (cd/m²) | Efficiency (lm/w) |
|---|---|---|---|---|---|
| 11 | 23 | 6 | 2140 | 11230 | 1.38 |
| 12 | 47a | 6 | 1970 | 10140 | 1.30 |
| 13 | 61a | 6 | 2230 | 12500 | 1.43 |
| 14 | 74a | 5 | 2180 | 14200 | 1.58 |

Example 15

A device was prepared in a similar manner as in Example 3 except for providing a light-emitting layer having a thickness of 20 nm by co-depositing the above exemplified compound No. 23 and the above exemplified compound No. 120 (4:100 by weight) as a light-emitting layer 3.

Using an ITO electrode 2 as a positive electrode and an Al—Li electrode 4 as a negative electrode, a voltage of 4 V was applied to the device thus obtained, so that a light emission having an emission brightness of 1100 cd/m², a maximum brightness of 27700 cd/m², and an emission efficiency of 2.25 lm/W was observed.

Examples 16 to 18

Devices were prepared and examined in a similar manner as in Example 15 except for using the compounds shown in Table 3 instead of the exemplified compound No. 23. The results are shown in Table 3.

TABLE 3

| Example | Exemplified Compound No. | Applied Voltage (V) | Brightness (cd/m²) | Maximum brightness (cd/m²) | Efficiency (lm/w) |
|---|---|---|---|---|---|
| 16 | 40a | 4 | 1240 | 27200 | 2.36 |
| 17 | 71b | 4 | 2150 | 30300 | 3.20 |
| 18 | 92a | 4 | 2670 | 32400 | 3.45 |

Examples 19 to 21

Devices were prepared and examined in a similar manner as in Example 15 except for using the compounds shown in Table 4 instead of the exemplified compound No. 120. The results are shown in Table 4.

TABLE 4

| Example | Exemplified Compound No. | Applied Voltage (V) | Brightness (cd/m²) | Maximum brightness (cd/m²) | Efficiency (lm/w) |
|---|---|---|---|---|---|
| 19 | 129 | 4 | 3720 | 34300 | 3.65 |
| 20 | 130 | 4 | 3800 | 33100 | 3.62 |
| 21 | 132 | 4 | 3350 | 31600 | 3.24 |

Example 22

A device was prepared in a similar manner as in Example 10 except for providing a light-emitting layer having a thickness of 20 nm by co-depositing the above exemplified compound No. 23 and the above exemplified compound No. 120 (4:100 by weight) as a light-emitting layer 3.

Using an ITO electrode 2 as a positive electrode and an Al—Li electrode 4 as a negative electrode, a voltage of 4 V was applied to the device thus obtained, so that a light emission having an emission brightness of 1890 cd/m², a maximum brightness of 29200 cd/m², and an emission efficiency of 2.501 lm/W was observed.

Examples 23 to 25

Devices were prepared and examined in a similar manner as in Example 15 except for using the compounds shown in Table 5 instead of the exemplified compound No. 23. The results are shown in Table 5.

TABLE 5

| Example | Exemplified Compound No. | Applied Voltage (V) | Brightness (cd/m²) | Maximum brightness (cd/m²) | Efficiency (lm/w) |
|---|---|---|---|---|---|
| 23 | 43a | 4 | 1950 | 28900 | 2.66 |
| 24 | 49a | 4 | 2350 | 34200 | 3.53 |
| 25 | 61a | 4 | 3100 | 32300 | 3.45 |

Examples 26 to 28

Devices were prepared and examined in a similar manner as in Example 15 except for using the compounds shown in Table 6 instead of the exemplified compound No. 120. The results are shown in Table 6.

TABLE 6

| Example | Exemplified Compound No. | Applied Voltage (V) | Brightness (cd/m²) | Maximum brightness (cd/m²) | Efficiency (lm/w) |
|---|---|---|---|---|---|
| 26 | 129 | 3 | 500 | 38300 | 5.64 |
| 27 | 130 | 3 | 530 | 39100 | 5.68 |
| 28 | 132 | 3 | 470 | 34700 | 4.20 |

Example 29

A voltage was applied to the device produced in Example 26 for 100 hours with the current density kept at 7.0 mA/cm² in a nitrogen atmosphere. As a result, the initial brightness was 400 cd/m² and the brightness after 100 hours was 380 cd/M² and thus deterioration in brightness was small.

Examples 30 to 34

The emission spectra of the devices produced in Examples 4, 5, 11, 19, and 22 were observed by using MCPD-7000 and the CIE chromaticity coordinates were measured. The results are shown in Table 7.

TABLE 7

| Example | Example of devices | CIE chromaticity coordinates (x, y) |
|---|---|---|
| 30 | 4 | 0.15, 0.13 |
| 31 | 5 | 0.15, 0.12 |
| 32 | 11 | 0.15, 0.12 |
| 33 | 19 | 0.15, 0.11 |
| 34 | 22 | 0.15, 0.11 |

Comparative Example 1

A device was produced in a similar manner as in Example 10 except for using the following comparative compound in a light-emitting layer 3.

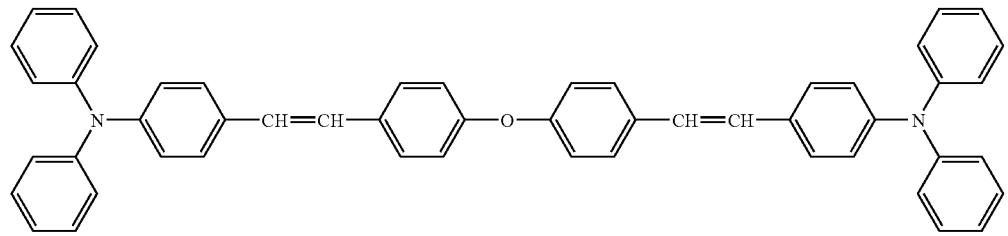

Using an ITO electrode 2 as a positive electrode and an Al—Li electrode 4 as a negative electrode, a voltage of 6 V was applied to the device thus obtained, so that a light emission having an emission brightness of 940 cd/m², a maximum brightness of 5050 cd/m², and an emission efficiency of 0.63 lm/W was observed.

In addition, the emission spectrum of this device was observed with MCPD-7000 and CIE chromaticity coordinates were measured. The result was (x, y)=(0.16, 0.29).

Comparative Example 2

A device was prepared in a similar manner as in Example 10 except for providing a light-emitting layer 3 having a thickness of 20 nm by co-depositing the above comparative compound and the above exemplified compound No. 129 (4:100 by weight) as a light-emitting layer 3.

Using an ITO electrode 2 as a positive electrode and an Al—Li electrode 4 as a negative electrode, a voltage of 6 V was applied to the device thus obtained, so that a light emission having an emission brightness of 1060 cd/m², a maximum brightness of 9270 cd/m², and an emission efficiency of 0.82 lm/W was observed.

In addition, the emission spectrum of this device was observed with MCPD-7000 and CIE chromaticity coordinates were measured. The result was (x, y)=(0.16, 0.27).

INDUSTRIAL APPLICABILITY

As explained above, organic light-emitting devices using the compounds represented by the general formula (1) exhibit extremely pure luminescent hue, and have light emission characterized by high efficiency, high brightness, and long lifetime. In particular, an organic layer containing the compound represented by the general formula (1) is excellent as a light-emitting layer.

Moreover, the devices can be produced by the use of vacuum vapor deposition method, casting method or the like. Large-area devices, therefore, can be produced at a relatively low cost.

What is claimed is:

1. An oligofluorenylene compound represented by the following formula 40a or formula 71b:

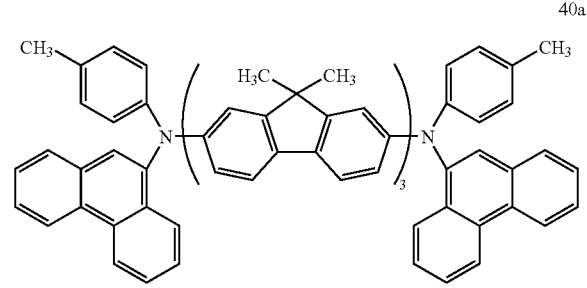

-continued

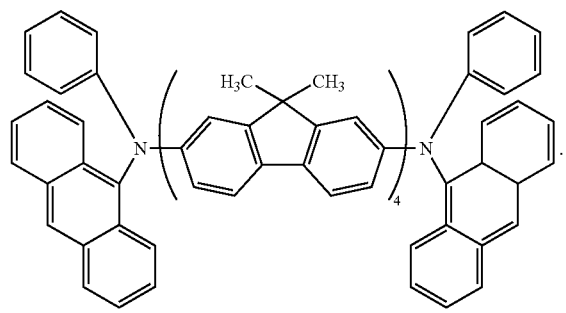

71b

2. An organic light-emitting device comprising:
a pair of electrodes comprising an anode and a cathode; and
a light-emitting layer comprising an organic compound, which is sandwiched between the electrodes, wherein the light-emitting layer comprises the oligofluorenylene compound according to claim 1.

3. An organic light-emitting device comprising:
a pair of electrodes comprising an anode and a cathode; and
a light-emitting layer comprising an organic compound, which is sandwiched between the electrodes, wherein the light-emitting comprises a host material and a dopant material, and the dopant material comprises the oligofluorenylene compound according to claim 1.

* * * * *

UNITED STATES PATENT AND TRADEMARK OFFICE
CERTIFICATE OF CORRECTION

| | | |
|---|---|---|
| PATENT NO. | : 7,229,702 B2 | |
| APPLICATION NO. | : 10/506300 | |
| DATED | : June 12, 2007 | |
| INVENTOR(S) | : Akihito Saitoh et al. | |

It is certified that error appears in the above-identified patent and that said Letters Patent is hereby corrected as shown below:

ON TITLE PAGE AT (73) ASSIGNMENT

"Tokyp (JP)" should read --Tokyo (JP)--.

UNITED STATES PATENT AND TRADEMARK OFFICE
CERTIFICATE OF CORRECTION

PATENT NO. : 7,229,702 B2  
APPLICATION NO. : 10/506300  
DATED : June 12, 2007  
INVENTOR(S) : Akihito Saitoh et al.

Page 2 of 3

It is certified that error appears in the above-identified patent and that said Letters Patent is hereby corrected as shown below:

COLUMN 96

Lines 25-40, "

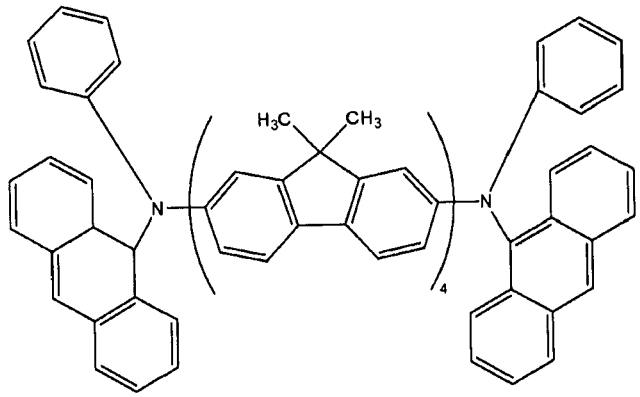

"

should read

--

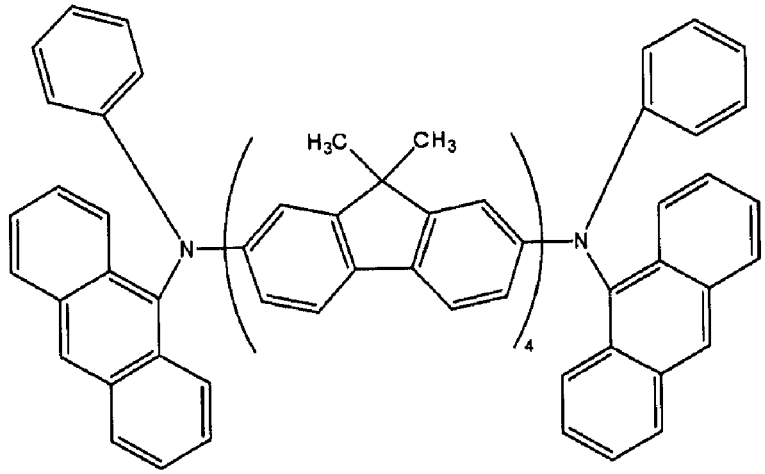

--.

UNITED STATES PATENT AND TRADEMARK OFFICE
CERTIFICATE OF CORRECTION

| | |
|---|---|
| PATENT NO. | : 7,229,702 B2 |
| APPLICATION NO. | : 10/506300 |
| DATED | : June 12, 2007 |
| INVENTOR(S) | : Akihito Saitoh et al. |

It is certified that error appears in the above-identified patent and that said Letters Patent is hereby corrected as shown below:

<u>COLUMN 104</u>

Line 13, "light-emitting" should read --light-emitting layer--.

Signed and Sealed this

Twenty-seventh Day of May, 2008

JON W. DUDAS
*Director of the United States Patent and Trademark Office*